US005691460A

United States Patent [19]

Duvic et al.

[11] Patent Number: 5,691,460
[45] Date of Patent: Nov. 25, 1997

[54] EPIDERMAL SURFACE ANTIGEN GENE

[75] Inventors: Madeleine Duvic; Wanda T. Schroeder, both of Houston, Tex.

[73] Assignee: The University of Texas System, Austin, Tex.

[21] Appl. No.: 279,270

[22] Filed: Jul. 22, 1994

Related U.S. Application Data

[63] Continuation-in-part of Ser. No. 956,841, Oct. 1, 1992, abandoned.

[51] Int. Cl.$^6$ .......................... C07H 21/02; C07H 21/04
[52] U.S. Cl. ........................................ 536/23.2; 536/23.5
[58] Field of Search .............................. 536/23.1, 24.3, 536/23.5, 23.2

[56] References Cited

FOREIGN PATENT DOCUMENTS

WO 94/07906  4/1994  WIPO.

OTHER PUBLICATIONS

Maniatis., Molecular Cloning., vol. 3, p. 17.10 (1989).
Green et al., Nucleic Acid Res 16(1):369 (1988) "A Versatile In Vivo and In Vitro . . . ".
Spoerel et al., Methods Enzymol 152:588–597 (1987) "Identification of Genomic Sequences . . . ".
Schroeder et al, J.B.C 269:19983–19991 (1994).
Mandavilli et al., (1992), Clinical Research, 40(4), "Expression of Epidermal Surface Antigen in Non–Epithelial Cells Result in Morphological Transformation".
Cho et al. (1992), Clinical Research, 40(4), "Epidermal Surface Antigen mRNA and Protein Expression in Melanocytes and Meloma Lines In Vitro".
Annarella et al. (1992), Clinical Research, 40(4), "Expression of Epidermal Surface Antigen mRNA and Protein in Cultured Keratinocytes and hyperproliferative Disorders".
Annarella et al. (1992), Clinical Research, 40(4):800A, "Triplex Binding of Oligonucleotides for the Epidermal Growth Factor Promoter–Binding and Effects In Vitro".
Chema et al. (1992), Clinical Research, 40(4):800A, "Cloning, Mapping, and Expression of the Mouse Epidermal Surface Antigen (ESA) cDNA".
Kayes et al. (1992), Genomics, 14:369–376, "The Gene for a Novel Epidermal Antigen Maps near the Neurofibromastosis 1 Gene".
Amagai et al., "Autoantibodies against a Novel Epithelial Cadherin in Pemphigus Vulgaris, a Disease of Cell Adhesion," Cell, 67:869–877, 1991, published in USA.
Beutner et al., "Autoantibodies in Pemphigus Vulgaris," JAMA, 192(8):98–104, 1965, published in USA.
Beutner et al., "The Immunopathology of Pemphigus and Bullous Pemphigoid," Journal of Investigative Dermatology, 51(2):63–80, 1968, published in USA.
Burridge et al., "Focal Adhesions: Transmembrane Junctions Between the Extracellular Matrix and the Cytoskeleton," Ann. Rev. Cell Biol., 4:487–525, 1988, published in USA.

Davis, L.G. et al., "Guanidine Isothiocyanate Preparation of Total RNA," section 11–1., pp. 130–135, 1986, in Basic Methods in Molecular Biology, eds. Davis, L.G., Debner, M.D. and Battery, J.F. (Elsevier Science Pub., New York), 1st Edition, published in USA.
Devereux et al., "A Comprehensive Set of Sequence Analysis Programs for the VAX," Nucleic Acids Research, 12(1):387–395, 1984, published in Europe.
Garrod, D.R., "Desmosomes, Cell Adhesion Molecules and the Adhesive Properties of Cells in Tissues," J. Cell Sci. Suppl., 4:221–237, 1986, published in the United Kingdom.
Harper and Marselle, "RNA Detection and Localization in Cells and Tissue Sections by in Situ Hybridization of $^{35}$S–Labeled RNA Probes," Methods in Enzymology, 151:539–551, 1987, published in USA.
Hashimoto et al., "The Ultrastructure of the Skin of Human Embryos," The Journal of Investigative Dermatology, 47(4):317–335, 1966, published in USA.
Horwitz et al., "Interaction of Plasma Membrane Fibronectin Receptor with Talin–A Transmembrane Linkage," Nature, 320:531–533, 1986, published in the United Kingdom.
Jordan et al., "Direct Immunofluorescent Studies of Pemphigus and Bullous Pemphigoid," Arch. Derm., 103:486–491, 1971, published in USA.
Katz et al., "Cell Adhesion Molecules: Structure, Function, and Implication in a Variety of Cutaneous and Other Pathologic Conditions," International Journal of Dermatology, 30(3):153–160, 1991, published in USA.
Kozak, Marilyn, "An Analysis of 5'–Noncoding Sequences from 699 Vertebrate Messenger RNAs," Nucleic Acids Research, 15(20):8125–8148, 1987, published in Europe.
Kayes et al., "The Gene for a Novel Epidermal Antigen Maps near the Neurofibromatosis 1 Gene," Genomics, 14:369–376, 1992, published in USA.
Korman et al., "Demostration of an Adhering–Junction Molecule (Plakoglobin) in the Autoantigens of Pemphigus Foliaceus and Pemphiqus Vulgaris," The New England Journal of Medicine, 321(10):631–635, 1989, published in USA.

(List continued on next page.)

Primary Examiner—Eggerton A. Campbell
Attorney, Agent, or Firm—Denise L. Mayfield, Es

[57] ABSTRACT

The present invention relates to the cloning, sequencing and characterization of a unique human epidermal surface antigen, ESA, and to methods for preparing and using the ESA gene and protein. The ESA gene is mapped to the region 17q11-12, on the long arm of chromosome 17, in the same area as the NF1 locus (the gene for von Recklinghausen neurofibromatosis). The mouse ESA has been located to chromosome 11. ESA mRNA is expressed in cultured keratinocytes and melanocytes, as well as in several carcinoma cell lines. Methods employing the antigen and/or DNA segments in diagnostic and therapeutic methods, including gene therapy, for the treatment of a variety of diseases, including cancer and autoimmunity, are disclosed. Methods for targeting molecules to the suprabasal epidermal cell layer are also presented.

17 Claims, 8 Drawing Sheets

OTHER PUBLICATIONS

Kyte and Doolittle, "A Simple Method for Displaying the Hydropathic Character of a Protein," *J. Mol. Biol.*, 157:105–132, 1982, published in the United Kingdom.

Matsunaka and Mishima, "Electron Microscopy of Embryonic Human Epidermis at Seven and Ten Weeks," *Acta Derm.–Venereol.*, 49:241–250, 1969, published in Europe.

Merlob et al., "Neonatal Pemphigus Vulgaris," *Pediatrics*, 78(6):1102–1105, 1986, published in USA.

Negi et al., "Monoclonal Antibody to a 35 kD Epidermal Protein Induces Cell Detachment," *J. Invest. Dermatol.*, 86:634–637, 1986, published in USA.

Sams and Jordon, "Correlation of Pemphigoid and Pemphigus Antibody Titres with Activity of Disease," *Br. J. Derm.*, 84:7–13, 1971, published in Europe.

Sanger et al., "DNA Sequencing with Chain–Terminating Inhibitors," *Proc. Natl. Acad. Sci. USA*, 74(12):5463–5467, 1977, published in USA.

Schiltz and Michel, "Production of Epidermal Acantholysis in Normal Human Skin in Vitro by the IgG Fraction from Pemphigus Serum," *The Journal of Investigative Dermatology*, 67(2):254–260, 1976, published in USA.

Schroeder et al., "The Gene for an Epidermal Surface Antigen is in Close Proximity to the Locus for Von Recklinghausen Neurofibromatosis," *Society for Investigative Dermatology Abstract Form–Clinical Research*, Sep. 20, 1990, printed in USA.

Schroeder et al., "The Human Gene for an Epidermal Surface Antigen (M1751) is Located at 17q11–12," *Genomics*, 11:481–482, 1991, published in USA.

Southern, E.M., "Detection of Specific Sequences Among DNA Fragments Separated by Gel Electrophoresis," *J. Mol. Biol.*, 98:503–517, 1975, published in the United Kingdom.

Stanley et al., "Isolation of Complementary DNA for Bullous Pemphigoid Antigen by Use of Patients' Autoantibodies," *The Journal of Clinical Investigation*, 82:1864–1870, 1988, published in USA.

Tanaka et al., "Comparison of Molecularly Cloned Bullous Pemphigoid Antigen to Desmoplakin I Confirms That They Define a New Family of Cell Adhesion Junction Plaque Proteins," *The Journal of Biological Chemistry*, 266(19):12555–12559, 1991, published in USA.

Tokunaga et al., "Enhanced Expression of a Glyceraldehyde–3–Phosphate Dehydrogenase Gene in Human Lung Cancers," *Cancer Research*, 47:5616–5619, 1987, published in USA.

Weinberger et al., "Identification of Human Glucocorticoid Receptor Complementary DNA Clones by Epitope Section," *Science*, 228:740–742, 1985, published in USA.

Wood and Beutner, "Blocking–Immunofluorescence Studies on the Specificity of Pemphigus Autoantibodies," *Clinical Immunology and Immunopathology*, 7:168–175, 1977, published in USA.

Young and Davis, "Efficient Isolation of Genes by Using Antibody Probes," *Proc. Natl. Acad. Sci. USA*, 80:1194–1198, 1983, published in USA.

Young and Davis, "Yeast RNA Polymerase II Genes: Isolation with Antibody Probes," *Science*, 222:778–782, 1983, published in USA.

Brutlag et al., "Improved Sensitivity of Biological Sequence Database Searches," *CABIOS*, 6(3):237–245, 1990, published in UK.

PCT/US93/09309, PCT Search Report, Dec. 27, 1993.

Length: 290

```
MTLQPRCEDV ETAEGVALTV TGVAQVKIMT EKELLAVACE QFLIGLNVQDI         50
KNVVLQTLEG HLRSILGTLT VEQIYQDRDQ FAKLVREVAA PDVGRMGIEI        100
LSFTIKDVYD KVDYLSSLGK TQTAVVQRDA DIGVAEAERD AGIREAECKK        150
EMLDVKDMAD TKIADSKRAF ELQKSAFSEE VNIKTAEAQL AYELQGAREQ        200
QKIRQEEIEI EVVQRKKQIA VEAQEILRTD KELIATVRRP AEAEAHRIQQ        250
IAEGEKVKQV LLAQAEAEKI RKIGEAERQS SRRWARQRLSG                  290
```

FIG.1

| | |
|---|---|
| CGGCCCAACG AGGCGCTGGT GGTTTCAGGG GGCTGTTGTG GTTCCGACTA | 50 |
| TAAACAGTAC GTGTTTGGCG GCTGGGCCTG GGCCTGGTGG TGTATCTCCG | 100 |
| ACACTCAGAG GATTTCCCTA GAGATTATGA CGTTGCAGCC CCGCTGCGAG | 150 |
| GACGTAGAGA CGGCCGAGGG GGTAGCTTTA ACTGTGACGG GTGTCGCCCA | 200 |
| GGTGAAGATC ATGACGGAGA AGGAACTCCT GGCCGTGGCT TGTGAGCAGT | 250 |
| TTCTGGGTAA GAATGTGCAG GACATCAAAA ACGTCGTCCT GCAGACCCTG | 300 |
| GAGGGACATC TGCGCTCCAT CCTCGGGACC CTGACAGTGG AGCAGATTTA | 350 |
| TCAGGACCGG GACCAGTTTG CCAAGCTGGT GCGGGAGGTG GCAGCCCCTG | 400 |
| ATGTTGGCCG CATGGGCATT GAGATCCTCA GCTTCACCAT CAAGGACGTG | 450 |
| TATGACAAAG TGGACTATCT GAGCTCCCTG GGCAAGACGC AGACTGCCGT | 500 |
| GGTGCAGAGA GATGCTGACA TTGGCGTGGC CGAGGCTGAA CGGGACGCAG | 550 |
| GCATCCGGGA AGCTGAGTGC AAGAAGGAGA TGCTGGATGT GAAGTTCATG | 600 |
| GCAGACACCA AGATTGCTGA CTCTAAGCGA GCCTTCGAGC TGCAAAAGTC | 650 |
| AGCCTTCAGT GAGGAGGTTA ACATCAAGAC AGCTGAGGCC CAGTTGGCCT | 700 |

FIG.2A

```
ATGAGCTGCA GGGGGCCCGT GAACAGCAGA AGATCCGGCA GGAAGAGATT      750

GAGATTGAGG TTGTGCAGCG CAAGAAACAG ATTGCCGTGG AGGCACAGGA      800

GATCCTGCGT ACGGACAAGG AGCTCATCGC TACAGTGCGC CGGCCTGCCG      850

AGGCCGAGGC CCACCGCATC CAGCAGATTG CCGAGGGTGA AAAGGTGAAG      900

CAGGTCCTCT TGGCACAGGC AGAGGCTGAG AAGATCCGCA AAATCGGGGA      950

GGCGGAACGG CAGTCATCGA GGCGATGGGC AAGGCAGAGG CTGAGCGGAT     1000

GAAGCTCAAG GCAGAAGCCT ACCAGAAATA CGGGGATGCA GCCAAGATGG     1050

CCTTGGTGCT AGAGGCCCTG CCCCAGATTG CTGCCAAAAT CGCTGCCCCA     1100

CTTACCAAGG TCGATGAGAT TGTGGTCCTC AGTGGAGACA ACAGTAAGGT     1150

CACATCAGAA GTGAACCGAC TGCTGGCCGA GCTGCCTGCC TCTGTGCATG     1200

CCCTCACAGG CGTGGACCTG TCTAAGATAC CCCTGATCAA GAAGGCCACT     1250

GGTGTGCAGG TGTGAGGCTC CTACAGGCCC ACTCTCTTCA GCAGCCACCC     1300

GGCCCTCCCT CCAGCACCCG TTTTAATCCC ACAGAACAAC GGGAACGTTA     1350

CTGACTCTGG TGCCTTATCT CGAAGGGACC AGAAGTGCTG CGTGTTCAGG     1400

CCATCTCTGG CTGTCTTCCT GTCTCTCCTG TCTGTCCACC TCCTCCTCTT     1450

CCTCTCCTTT ACCCCACTTT CACTGCCACT TTCATCAGGT TTGTGTCTCA     1500

TCTCCCTGCC TGTCTTTTCC TTTGTCTGTC TTTTTCTTTC CCCCATGCAC     1550

ATCATGTAGA TTAAGCTGAA GATGTTTATT ACAATCACTC TCTGTGGGGG     1600
```

FIG.2B

```
GTGGCCCTGC TGCTCCTCAG AATCCTGGTG CCTTGAAGTT CTCTGTGCAT      1650

CTGTCCATCC TCCCTATGGC CCTGGCCAGA GCTCAGCATG GGCAGGGGTT      1700

CTGGGTAGGA CGGTCACTGT CCTCTCTCCT GGACTGGTCT TCCCAGCCCT      1750

AAACCCTGCC CCAGGAAGCC CACAGCCTCA CCTGCTGCTG CCCCTCTAGG      1800

TCTGGGCAGC CATGACCTGC AGGGCCCAGA GACACTGTCC TTCCCCTCAT      1850

CCACCCAAGG CCCCAGCCAG CGCTCATACC CTGTCCTTTC TCCCTGACCC      1900

CAAGGGCACA GAGGCAAGGC CTCCTGTCTA CAGCAGCTTC CTCAGTTTCC      1950

TACTGCCTTA GGAGGCCCCT GCTTGTGCTC AGGGAAGGCC TCTTCATGGG      2000

CATGTTCCTG CTGGGGCGGT GCGGTTTGGT CCCAACTCTG CTAAGTTTTC      2050

TGAGATGAGG GTCTAGCCCT GTTGGGGACA GAAAAGTGTG TAGACCTTCT      2100

TCCTGCTAGG GCTGCACTGT CCTGGGTGTT GGGCCCTTCT GGTGGACAAG      2150

GCTGTGCCAA CCCTGTACAG AATCGAGTGC TGTAGCCTGG CCAGACCCCA      2200

GAGCCCTTGT GCCATCTTTC TTCCTGGCCA GAGTGATGGG GTTCCAGCCA      2250

TGGGGAAGCA ACCCAATCCT CTGTCTCCTT GCTCCAATGG AGGCAGAAGA      2300

GCCCAGGACC CAAGCGTCTT GGCAGGGGTG CTGTGAATGT CCAGTGGTCC      2350

CAGCTCCCCA CCCTGGCCCT GCCCCAGCCT GTGTAGCTCT TCCTGCATGT      2400

GGATGCTGCA TGTCTGGTCT GGGGCTTGGA TGTTGCACTG CCCCACTGCC      2450

TGTCCCTTCT GGTAAAATAA AGAACTCTTA ATGCCCG                    2487
```

FIG.2C

EPIDERMAL SURFACE ANTIGEN GENE

This application is a continuation in part of application Ser. No. 07/956,841, filed Oct. 1, 1992 abandoned.

The government has rights in the present invention as research relevant thereto was supported by NIH Grants AR-36546 and AR-40520.

BACKGROUND OF THE INVENTION

1. Field of the Invention

The present invention relates generally to molecular biology, and its application to the cloning of human tissue-specific markers or antigens. In particular, the invention relates to the cloning, sequencing, characterization and chromosomal mapping of a human epidermal surface antigen (ESA). This antigen, and its encoding DNA sequences, will have utility in, for example, chromosomal mapping and analyses, specific tumor screening and diagnosis, and in gene therapy. Accordingly, the present invention provides improved diagnostic or therapeutic methods relating to various diseases or disorders related to ESA, including, for example, neurofibromatosis 1, autoimmune and congenital bullous diseases, Ehlers-Danlos disease, and cancers such as malignant schwannomas and melanomas and other neural crest tissue cancers.

2. Description of the Related Art

Several proteins are present on the surface of epidermal cells. Many of these antigens are generally recognized as important for normal epidermal maintenance and function. This general recognition is based on the involvement of these cell-surface antigens in several diseases, particularly genetic diseases, that manifest in abnormal epidermal cell adhesion, the autoimmune bullous diseases[1-4], as well as in diseases characterized by abnormal skin differentiation, such as psoriasis, squamous cell carcinoma, basal cell carcinoma, and cytoskeletal diseases, such as epidermolysis, bullosa simplex, Dahiers disease, and familial peray shigus.

The autoimmune bullous diseases include bullous pemphigoid, pemphigus vulgaris and foliaceus. In these diseases, autoantibodies bind to normal epidermal cell-surface molecules resulting in cell disadherence and ultimately blister formation.[5-8] Hence, it has been postulated that the antigens involved in autoimmune bullous disease are important for epidermal cell adhesion. These diseases are known to be inherited from generation to generation. However, because the characterization of the gene that encodes the antigen responsible for the manifestation of these diseases has not yet be discerned, methods for genetically screening for these diseases do not currently exist.

Serum antibodies obtained from patients with autoimmune bullous disease have been used in the characterization of normal epidermal proteins involved in autoimmune bullous disease. A cDNA encoding the bullous pemphigoid antigen has been isolated and demonstrated to have sequence and structural homology with desmoplakin I, a desmosomal plaque protein.[9,10] The pemphigus vulgaris antigen shares significant homology with members of the cadherin family of $Ca^{2+}$-dependent cell adhesion molecules, especially desmoglein I.[11] Autoantibodies against an adherent junction protein, plakoglobin, have been detected in patients with pemphigus foliaceus and pemphigus vulgaris[12].

The present inventors recently developed hybridomas which secrete antibodies against antigens present on cultured human keratinocytes. One of these monoclonal antibodies, termed ECS-1, was found to stain the nucleated layers of human epidermis in an intercellular pattern, and to react, in Western blotting studies, with a specific protein extracted from neonatal foreskin epidermis and cultured human keratinocytes (Schroeder et al., (1991)) Genomics, 11:481–482. The target antigen was determined to have an apparent molecular weight on SDS/PAGE of approximately 35 kDa. This ECS-1 monoclonal antibody was also found to cause cell detachment in vitro, and the addition of ECS-1 directly to cultured mouse keratinocytes was observed to result in cell detachment which was enhanced by the presence of complement.

Human chromosome 17, specifically the long arm of chromosome 17, is known to contain the gene for neurofibromatosis 1 (NF1).[14,15] However, no other genes that map in, or adjacent to, this region are currently known. The identification of additional genes near this region, and preferably a gene that did not demonstrate recombination with the neurofibromatosis gene, would greatly enhance the diagnostic value of genetic screening for this disease and other disorders related to changes in chromosome 17.

A number of adhesion proteins including integrins, CAMs, cadherins, plakoglobin, and the desmosomal proteins desmoglein, desmoplakin, and desmocollin have been isolated and are also known to play a role in epidermal cell adhesion.[31-33] Intracellular accessory molecules such as talin and vinculin are known to act as transmembrane linkages in focal adhesion.[34,35] Therefore, it is reasonable to postulate that still unknown, relatively small molecular weight extracellular accessory proteins exist. In recent years a number of genes for epidermal surface proteins have been isolated. However, the function of these proteins and the molecular mechanisms involved in their tissue-specific expression remain unknown.

The isolation of further epidermal-specific genes will allow the mechanisms underlying specific elements of epidermal cell function to be elucidated. Such events include, for example, the interaction of epidermal proteins with other epidermal molecules or extracellular matrix proteins, and how such interactions govern cell adhesion, cell signalling, cell differentiation and epidermal gene expression. The delineation of factors involved in the regulation and expression of genes important to normal epidermal cell function, will ultimately lead to an understanding of the mechanisms underlying epidermal cell abnormalities and pathologies. Aberrant epithelial cell function, particularly regarding surface antigens, is known to be involved in many hyperproliferative and malignant disorders. Thus, isolation of an antigen associated with malignant epidermal diseases would be useful in the detection and treatment of malignancies of melanocytes and epithelial cells.

The molecular cloning and characterization of genes encoding epidermal cell surface antigens is thus of significant clinical importance, as it would allow new diagnostic and therapeutic approaches to various epidermal diseases to be developed. For example, the availability of epithelial cell surface antigen DNA sequences would open up new genetic screening methods for the detection of specific epidermal surface protein deficiencies, or for the diagnosis of malignant schwannomas, melanomas and other neural crest tissue cancers. It would also facilitate the development of new gene therapy protocols for treating epithelial cell disorders, including cancer and Ehlers-Danlos disease.

The availability of epithelial cell surface proteins themselves would also have clinical importance. Access to such purified proteins would allow the mechanisms triggering the production of autoantibodies, for example, in autoimmune bullous diseases, to be elucidated. This would likely lead to new strategies to control antibody and disease development. Furthermore, from a knowledge of protein structure and function, effective pharmacological agents could be developed for the treatment of such autoimmune disorders, or indeed any disease in which epithelial cell dysfunction is involved.

SUMMARY OF THE INVENTION

By the molecular cloning and characterization of a human epidermal surface antigen, ESA, the present invention overcomes several of the drawbacks inherent in the prior art. The present invention also encompasses unique and useful epidermal surface antigen compositions, including genes, DNA sequences, purified proteins and antibodies. It also provides methods for the preparation of such compositions and methods for their utilization in, for example, diagnostic and therapeutic methods for the treatment of a variety of diseases, including cancer and autoimmune diseases. Methods for targeting molecules to the suprabasal epidermal cell layer are also presented, as are improved genetic screening and polymorphic marker systems for human chromosome 17.

The epidermal surface antigen (ESA) of the present invention may be characterized as having a molecular weight of about 41.5 kDa. In preferred embodiments, the ESA is human ESA and may be characterized as being normally expressed by differentiated epidermal cells, keratinocytes, melanoma cells or squamous cells; as being $Ca^{+2}$ independent; as having a high antigenicity and surface probability, and as having a hydrophobic N-terminal region of about 90–110 amino acids and a hydrophilic C-terminal region of about 180–200 amino acids. The ESA may be even further defined as including several regions with alternating hydrophilic and hydrophobic amino acids. Transfection of ESA into a fibroblast cell line by the present inventors resulted in a change in normal fibroblast cell morphology and in the establishment of cell-cell contact.

As used herein, the term $Ca^{+2}$ independent refers to a protein the expression of which is not regulated by extracellular $Ca^{++}$ levels in cultured keratinocytes. The antigen of the present invention, being $Ca^{+2}$ independent, may thus be distinguished from many other differentiation-specific genes and antigens of the epidermis. The ESA protein may also be characterized as being absent from undifferentiated basal cells in the epidermis, and therefore, as being linked to differentiation in vivo. The ESA is shown herein to play an important role in normal epidermal structure, function and most particularly, cell adhesion. For example, the inventors demonstrate that addition of ESA-1 mAb directly to epidermal cultures results in loss of cell adhesion.

Important aspects of the present invention concern isolated DNA segments and recombinant vectors encoding epidermal surface antigens, and particularly, the human epidermal surface antigen, and also the creation of recombinant host cells through the application of DNA technology, which express such an antigen.

As used herein, the term "DNA segment" in intended to refer to a DNA molecule which has been isolated free of total genomic DNA of a particular species. Therefore, a DNA segment encoding an epidermal surface antigen is intended to refer to a DNA segment which contains such coding sequences yet is isolated away from total genomic DNA of the species from which the DNA is obtained. Included within the term "DNA segment", are DNA segments which may be employed in the preparation of vectors, as well as the vectors themselves, including, for example, plasmids, cosmids, phage, viruses, and the like. Preferred cDNA constructs encoding an epidermal surface antigen in accordance with the present invention have been created and are designated pESA2.0 and pESA2.5.

In preferred embodiments, the invention concerns isolated DNA segments and recombinant vectors incorporating DNA sequences which encode a human epidermal surface antigen that includes within its amino acid sequence the amino acid sequence of SEQ ID NO:1, or a biologically functional equivalent thereof. The invention also concerns isolated DNA segments and recombinant vectors incorporating DNA sequences which encode a human epidermal surface antigen that includes within its nucleotide sequence the nucleotide sequence of SEQ ID NO:2, or a biologically functional equivalent thereof. Recombinant vectors and isolated segments may therefore include this coding region itself, coding regions bearing selected alterations or modifications in the basic coding region or may encode larger polypeptides which nevertheless include this coding region.

It will be understood that these aspects of the invention are not limited to the particular amino acid and nucleotide sequences of SEQ ID NO:1 and SEQ ID NO:2. Accordingly, nucleotide segments prepared in accordance with the present invention may also encode biologically functional equivalent proteins or peptides which have variant amino acid sequences. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. The concept of biological functional equivalents will be known to those of skill in the art, and is discussed in detail in Example 2.

The recombinant cloning of an epidermal surface antigen in accordance herewith was achieved through the use of the expression cloning employing antibodies. However, now that the nucleotide sequence information of the present invention is disclosed herein, oligonucleotides may be prepared and used for direct hybridization screening of further clone banks. In such screening methods, any type of clone bank, such as cDNA or genomic clone banks may be employed. Naturally, it is believed to be advantageous to employ cells such as differentiated epidermal cells, keratinocytes, melanoma cells or squamous cells, or even nonepidermal fibroblasts or diaphragm cells for the preparation of RNA from which the clone bank is to be generated.

The type of cDNA clone bank used in the screening procedure is not believed to be particularly critical. However, one will likely find particular benefit through the preparation and use of a phage-based bank, such as λgt10 or λgt11, preferably using a particle packaging system. Phage-based cDNA banks are preferred because of the large numbers of recombinants that may be prepared and screened with relative ease. The manner in which the cDNA itself is prepared is again not believed to be particularly crucial, however, oligo dT and randomly primed cDNA, may be advantageously used. Once a clone bank has been prepared, it may be screened in a number of fashions, as will be known to those of skill in the art in light of the present disclosure.

It is proposed that the DNA segments of the present invention may be employed for a variety of applications. For example, a particularly useful application concerns the recombinant production of the epidermal surface antigen, or fragments or subportions thereof. Additionally, DNA segments may also be used in the preparation of nucleic acid probes or primers, which can, for example, be used in the identification and cloning of related cDNAs, genes or related genomic sequences, or in the study of expression, and the like.

Turning firstly to the expression of the cloned antigen. Once a suitable (full length if desired) clone or clones have been obtained, whether they be cDNA based or genomic, they may be expressed in a recombinant host cell, to allow, for example, the recombinant preparation of the antigen. The engineering of DNA segment(s) for expression in a prokaryotic or eukaryotic system may be performed by techniques generally known to those of skill in recombinant expression.

As used herein, the term "engineered" or "recombinant" cell is intended to refer to a cell into which a recombinant gene, such as a gene encoding a epidermal surface antigen has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA gene (i.e., they will not contain introns), a copy of a genomic gene, or will include genes positioned adjacent to a promoter not naturally associated with the particular introduced gene.

Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the inventor does not exclude the possibility of employing a genomic version of a particular gene where desired.

It is believed that virtually any system may be employed, to express an epidermal surface antigen in accordance herewith, but it is envisioned that bacterial expression systems may ultimately be preferred, due to the ease of use and quantity of materials obtained thereby. Both cDNA and genomic sequences are suitable for eukaryotic expression, as the host cell will process the genomic transcripts to yield functional mRNA for translation into protein.

Almost any eukaryotic expression system may be utilized for the expression of epidermal surface antigens, e.g., baculovirus-based, glutamine synthase-based or dihydrofolate reductase-based systems could be employed. However, plasmid vectors incorporating an origin of replication and an efficient eukaryotic promoter, as exemplified by the eukaryotic vectors of the pCMV series, may be preferred. Other recombinant vectors that may be used include pGEX, retroviral vectors and SV40, among others. In any event, to effect expression, one would position the coding sequences adjacent to and under the control of the promoter. It is understood in the art that to bring a coding sequence under the control of such a promoter, one positions the 5' end of the transcription initiation site of the transcriptional reading frame of the protein between about 1 and about 50 nucleotides "downstream" of (i.e., 3' of) the chosen promoter.

Where eukaryotic expression is contemplated, one will also typically desire to incorporate into the transcriptional unit which includes the antigen, an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

It is contemplated that virtually any of the commonly employed host cells can be used in connection with the expression of epidermal surface antigens. Examples include cell lines typically employed for eukaryotic expression such as 239, AtT-20, HepG2, VERO, HeLa, CHO, WI 38, BHK, COS-7, RIN and MDCK cell lines.

Where bacterial expression is contemplated, it is well known in the art that *E. coli* is an ideal host cell. However, other cells may also be employed, such as, for example, bacilli such as *Bacillus subtilis*, or other enterobacteriaceae such as *Salmonella typhimurium* or *Serratia marcesans*, and various Pseudomonas, Baculovirus and yeast species may be used.

The DNA sequences disclosed herein will also find utility as probes or primers in nucleic acid hybridization embodiments. As such, it is contemplated that oligonucleotide fragments corresponding to the sequences of SEQ ID NO:2, for stretches of between about 10 nucleotides to about 30 nucleotides will find particular utility, with even longer sequences, e.g., 40, 50, 60, even up to full length, being even more particularly preferred. The ability of such nucleic acid probes to specifically hybridize to epidermal surface antigen-encoding sequences will enable them to be of use in a variety of embodiments. Most importantly, the probes can be used in a variety of assays for detecting the presence of complementary sequences in a given sample. However, other uses are envisioned, including the use of the sequence information for the preparation of mutant species primers, or primers for use in preparing other genetic constructions.

The use of a hybridization probe of about 10 nucleotides in length allows the formation of a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 nucleotides, or even longer where desired. Such fragments may be readily prepared by, for example, directly synthesizing the fragment by chemical means, by application of nucleic acid reproduction technology, such as the PCR technology of U.S. Pat. No. 4,603,102 (herein incorporated by reference) or by introducing selected sequences into recombinant vectors for recombinant production.

Accordingly, the nucleotide sequences of the invention may be used for their ability to selectively form duplex molecules with complementary stretches of epidermal surface antigen genes or cDNAs. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and\or high temperature conditions, such as provided by 0.02M–0.15M NaCl at temperatures of 50° C. to 70° C. Such selective conditions tolerate little, if any, mismatch between the probe and the template or target strand, and would be particularly suitable for isolating epidermal surface antigen genes, such as those encoding isoenzymes.

Of course, for some applications, for example, where one desires to prepare mutants employing a mutant primer strand hybridized to an underlying template or where one seeks to isolate epidermal surface antigen-encoding sequences from related species, functional equivalents, or the like, less stringent hybridization conditions will typically be needed in order to allow formation of the heteroduplex. In these circumstances, one may desire to employ conditions such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including radioactive, enzymatic or other ligands, such as avidin/biotin, which are capable of giving a detectable signal. In preferred embodiments, one will likely desire to employ an enzyme tag such a urease, alkaline phosphatase or peroxidase, instead of radioactive or other environmental undesirable reagents. In the case of enzyme tags, colorimetric indicator substrates are known which can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

In addition to DNA and nucleic acid segments, further molecular biological embodiments of the present invention concern genes encoding epidermal surface antigens, and more particularly, a gene encoding a human epidermal surface antigen. The present inventors have determined that a gene encoding human ESA is located on the long arm of chromosome 17, and more particularly, in the 17q11-12 region of chromosome 17. This localizes the ESA gene to the same general region as the neurofibromatosis-1 (NF1) locus, the gene for von Recklinghausen neurofibromatosis.

The ESA gene appears to be a single copy gene, with ESA mRNA and protein being expressed in differentiated epidermal cells, keratinocytes, melanoma cells or squamous cells. ESA mRNA is also expressed in non-epidermal fibroblasts and diaphragm, although these tissues are negative for ESA protein. The discordant expression of ESA protein and mRNA in basal epidermal cells, dermal fibroblasts, and diaphragm may be due to post-transcriptional or post-translational regulation.

The ESA gene appears to be well conserved in mammals, but is not present in amphibians or insects. For example, hybridization to genomic DNAs from dog, cat, rabbit, and mouse can be demonstrated under moderately stringent conditions. The presence of the ESA protein, and more particularly, the ESA epitope recognized by a monoclonal antibody (ECS-1), in mammalian species also demonstrates its well-conserved nature. Evidence of protein conservation among species is also presented by the fact that ECS-1 stains mouse and rabbit tissues with the same intensity as human epidermis. Therefore, it will be understood that epidermal surface antigens from all the above species fall within the scope of the present invention. However, nonmammalian species such as Xenopus and Drosophila do not contain ESA homologous sequences.

Owing to the localization of the human ESA gene to chromosome 17, the present invention also encompasses an improved polymorphic marker system for human chromosome 17, and consequently an improved method for human genetic screening of diseases traced to gene changes on human chromosome 17. Such diseases include, by way of example, neurofibromatosis 1, autoimmune bullous diseases, and indeed, any disease which one suspects may have be associated with an ESA (gene or peptide)-related abnormality.

RFLP SCREENING METHODS AND DIAGNOSTICS

In still another aspect of the invention, a method for detecting a restriction fragment length polymorphism of human chromosome 17 is provided. According to one embodiment, the method comprises obtaining a patient sample, isolating genomic nucleic acid from the sample, treating the genomic DNA with a restriction enzyme suitable for identifying a polymorphism in human chromosome 17 (such as restriction enzyme Pst 1 or other restriction enzyme) located at the 17q11-17q12 region, to provide restriction fragments, combining the restriction fragments with a nucleic acid fragment including a sequence essentially as set forth in SEQ ID NO:2, or a fragment thereof, and detecting the presence of restriction length fragment polymorphisms in the mixture. RFLP of chromosome 17 is characteristic of such diseases as epidermolysis, bullosa simplex, Dahiers, and Hailey-Hailey, and may thus be detected from the presence of a molecular change at the 17q11-12 chromosome region.

It is contemplated that there are over 200 restriction enzymes that could be used in the RFLP analysis systems for ESA gene of the present invention.

Pst 1 has been shown to be polymorphic for the ESA locus.[15] Thus, the inventors will prepare CA repeats for this locus by isolation of YAC clones from human chromosome 17.

Restriction length polymorphisms of chromosome 17 characteristic of such diseases as the autoimmune bullous diseases may thus be detected through analysis of the 17q11-12 chromosome region identified by the present inventors as included the ESA gene. Such a method is contemplated as the ESA gene is polymorphic in nature.

The RFLP method may also be used for determining gene linkage. Linkage for ESA with genetic diseases involving epidermal adhesion and morphology (Dahiers Hailey-Hailey, epidermolysis cellosa, psoriasis, and ictlyosis). Where linkage is found, the ESA gene may be studied at the DNA level. Samples that reveal a defect in the ESA protein will be identified, and patients given the purified ESA protein to correct and/or reduce the effects of the defect. Alternatively, gene therapy using the disclosed ESA gene (see SEQ ID NO:2) may be used as a potential cure for the ESA defect.

The present disclosure also demonstrates the early appearance of the ESA protein during embryonic development. The role of the ESA gene in epidermal cell adhesion is evidenced by its appearance at 9 weeks estimated gestational age in developing human skin. This first time of appearance is the same time that desmosomes first form.[13,29,30] The ESA protein is therefore postulated to be critical for the normal development of epithelial and epithelial-derived tissues in the developing embryo. It is anticipated by the present inventors that the isolated ESA gene may therefore be used in a method of gene therapy in utero for the correction of ESA-gene abnormalities.

Further aspects of the present invention concern an epidermal surface antigen, and particularly, a human epidermal surface antigen, purified relative to its natural state. The term "purified relative to its natural state", as used herein, is intended to refer to an epidermal surface antigen composition wherein the antigen is purified to any degree relative to its naturally-obtainable state, i.e., in this case, relative to its purity within epidermal cells. Accordingly, this refers to a composition comprising an epidermal surface antigen, from which has been removed various non-antigen components.

The preferred method for preparing an epidermal surface antigen is contemplated to include obtaining the antigen from a recombinant cell which one would culture under conditions effective to allow expression of the antigen. Most preferably, such recombinant host cells would be bacterial host cells, which may include, by way of example, *E. coli*, *H. influenzae*, Salmonella, Mycobacterium, or *Bacillus subtilis*. One would then collect the expressed antigen, which would even at this stage, be purified relative to its natural state, as is known to be the case for recombinantly expressed proteins in contract to those obtained from natural sources.

If desired, epidermal surface antigens obtained from recombinant cells may be further purified by subjecting the composition containing the antigen to one or more fractionation steps, for example, employing fractionation according to charge, hydrophobicity, size, and the like. The number of fractionation steps employed will generally be dependent on the degree of purification desired and the intended use of the resultant epidermal surface antigen, for example, clinical, analytical, antigenic, etc.

As mentioned above, although preferred for use in certain embodiments, there is no general requirement that the epidermal surface antigen always be provided in their most purified state. Indeed, it is contemplated that less substantially purified antigens will have utility in certain embodiments. These include, for example, analyzing their interaction with other epidermal or extracellular matrix proteins.

In still further embodiments, the present invention concerns an antibody having binding affinity for an epidermal surface antigen, and preferably, a human ESA, and even more preferably, a human ESA which includes within its amino acid sequence an amino acid sequence essentially as set forth in SEQ ID NO:1, or a biologically equivalent fragment thereof. Such antibodies may alternatively be monoclonal, or preferably, polyclonal antibodies.

Generally stated, the method for preparing the polyclonal antibody for ESA comprises administering an immunogen including an ESA peptide having an amino acid sequence of SEQ ID NO:1, or a fragment thereof, to an animal, providing booster treatments of the antigen to the animal until a detectable anti-ESA antibody titer level for antibody specific for the ESA antigen of SEQ ID NO:1 or a fragment thereof is detected; and isolating the anti-ESA antibody from a biological sample of the animal. According to one embodiment of the method, the animal in which the antibodies are raised is the rabbit. By way of example, polyclonal antibodies to ESA antigen fragments 1–238, 240–291, 193–207, and 277–291 have been prepared wherein those respective antigenic fragments are used as immunogen. The ESA antigen most preferably comprises a fragment of the ESA peptide of SEQ ID NO:1 that is found to be most highly conserved between the human and mouse ESA antigen.

Antibodies in accordance with the present invention may be employed in a variety of embodiments, such as, for example, for identifying an epidermal surface antigen within a sample. To achieve this, one would obtain a sample suspected of containing the antigen, contact the sample with the antibody, and then detect the presence of the antigen by testing for the presence of an immunocomplex, as will be known to those of skill in the art.

Kits for antigen detection are also encompassed by the present invention, and will generally include antibodies, immunodetection reagents, means for containing said antibodies and reagents, and even antigen preparations if desired. Immunodetection reagents will typically comprise a label associated with the antibody or antigen, or associated with a secondary binding ligand. Exemplary ligands might include a secondary antibody directed against the first antibody or antigen or a biotin or avidin (or streptavidin) ligand having an associated label. Of course, as noted above, a number of exemplary labels are known in the art and all such labels may be employed in connection with the present invention.

The container means will generally include a vial into which the antibody, antigen or detection reagent may be placed, and preferably suitably aliquoted. The kits of the present invention will also typically include a means for containing the antibody, antigen, and reagent containers in close confinement for commercial sale. Such containers may include injection or blow-molded plastic containers into which the desired vials are retained.

It is contemplated that embodiments of the invention for the screening of samples for antigen may also have application to non-clinical samples, such as in the titering of antigen or antibody samples, in the selection of hybridomas, and the like.

It is envisioned that epidermal surface antigens prepared in accordance with the present invention may be advantageously used in a number of different embodiments. For example, they may be used as antigens for testing for the presence of autoantibodies in the sera of patients suspected of having an autoimmune disorder, such as an autoimmune bullous disease.

The novel epidermal surface antigen proteins, genes and DNA segments of the present invention may also be employed in the treatment of a variety of different disease and disorders. For example, patients diagnosed as having the ESA gene defects, may be treated with compositions comprising epidermal surface antigens. These treatment aspects are particularly contemplated for treating autoimmune bullous diseases, such as in treating patients active pemphigus or bullous pemphigoid. It is contemplated that the administration of a pharmacologically effective amount of the ESA antigen described herein will facilitate binding of circulating ESA autoantibodies in the patient, thereby reducing the antibody available for binding to epidermal cell surface antigens in the animal, and thus reduce symptoms and/or progression of the disease in the patient.

The epidermal surface antigen be administered alone or in combination with pharmaceutically acceptable carriers, such as saline or a Ringer solution, in either single or multiple doses. For parenteral administration, including intravenous, intramuscular and subcutaneous injection, solutions of the inhibitor in various oils, emulsions, or aqueous sterile buffers may be employed. The precise compositions and use of such pharmaceutical carriers will be known to those of skill in the art in light of the present disclosure. For direct delivery of epidermal surface antigens to tissues, it is contemplated that the antigens may be given in a liposome-encapsulated form. Such techniques are known to increase the efficacy and significantly prolong the half-life of administered compounds. Liposome encapsulation can be accomplished in a number of manners, as will be known to those of skill in the art.

The ESA gene, cDNA or segments thereof may be used in gene therapy to treat epidermal cell-related pathologies in humans. DNA constructs encoding the human epidermal surface antigen may be targeted to human cells where they will direct the expression of the normal protein. Such DNA segments may be applied directly to cells, in the form of oligonucleotides, or other genetic constructs. It has been shown that oligonucleotides can successfully traverse cellular membranes. Other techniques for direct insertion in the cells include, by way of example, electroporation, or calcium phosphate transfection or lipofection. Oligonucleotides or DNA vectors could be packaged prior to administration to ensure stability their in circulation, for example, by liposome encapsulation. All such techniques related to gene therapy will be generally known to those of skill in the art.

The ESA antigen is demonstrated by the present inventors to be expressed only in suprabasal cell layers. This characteristic of the ESA gene renders the gene particularly useful in methods for targeting the delivery of particular agents and gene products to suprabasal cell layers in an animal. Such may be accomplished, for example, by isolating a promoter region of an ESA gene sequence, as defined in SEQ ID NO:2, preparing a recombinant vector with the ESA promoter region and a gene sequence encoding a substance to be delivered to a suprabasal layer of epidermal cells; and administering the vector to the animal; wherein the gene sequence encoding the substance to be delivered to the animal is selectively expressed in the suprabasal cell epidermal layers.

In addition to the gene therapy protocols outlined above, the specific delivery of other agents to the suprabasal layer of cells is contemplated. This is envisioned to be of use, for example, in the delivery of skin structural or adhesion proteins for differentiation (keratins, filaggrin, cytokines, hormones) for the treatment of genetic skin or other genetic deficiencies or diseases of abnormal differentiation, like psoriasis, icthyosis, E. bullos, Dahiens or Hailey-Hailey disease.

The following abbreviations are employed throughout the description of the present invention:

ESA=epidermal surface antigen mAb=monoclonal antibody

TBS=tris-buffered saline

PBS=phosphate-buffered saline cRNA=complementary RNA

IF=immunofluorescence surface probability=probability of finding antigen on surface Pst 1=a restriction enzyme useful for detecting the ESA RFLP.

BRIEF DESCRIPTION OF THE DRAWINGS

FIG. 1—Amino acid sequences of the ESA antigen (379 amino acid residues SEQ ID NO:1).

FIG. 2—Nucleic acid sequences encoding the ESA antigen (2488 nucleotide length SEQ ID NO:2).

DETAILED DESCRIPTION OF THE PREFERRED EMBODIMENTS

Figure 3A:
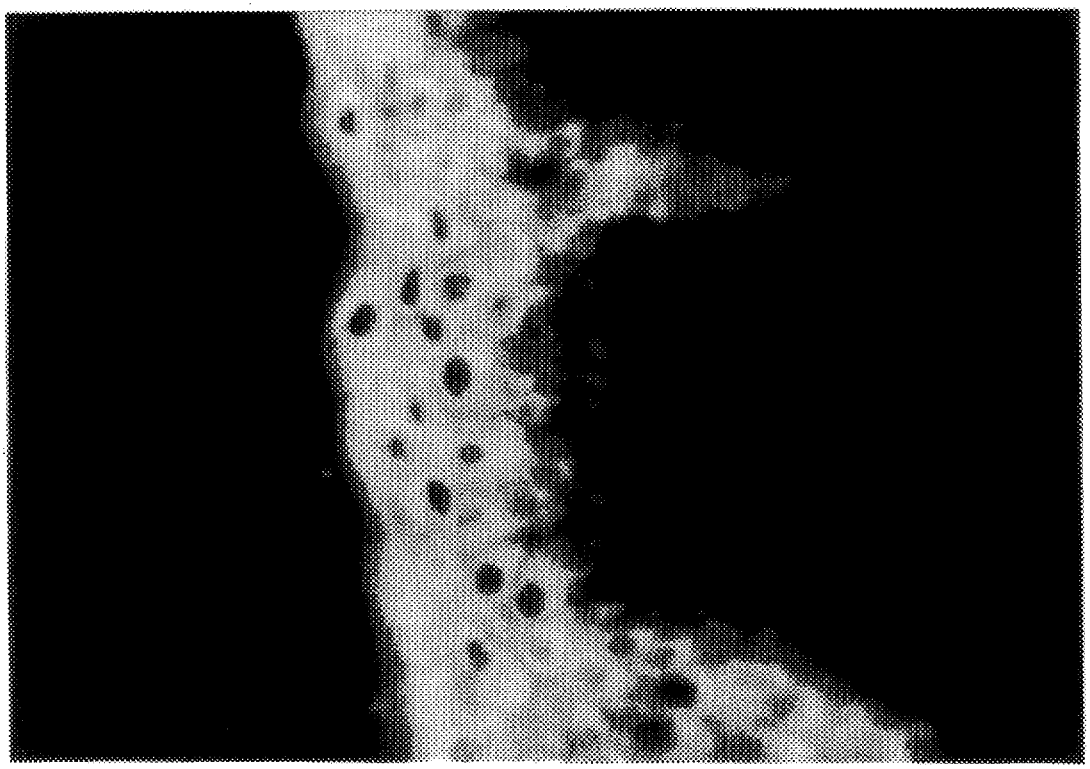
FIG. 3A and FIG. 3B—Indirect immunofluorescence of frozen skin sections with the ECS-1 antibody demonstrates staining throughout the epidermis with the exception of the basal cells. In situ hybridization of frozen skin sections probed with cRNA specific for ESA mRNA. Note that this mRNA is present in all layers of the epidermis including the basal cells.

Computer searches for protein or DNA sequence homologies with ESA were carried out using the programs WordSearch, Segments, and BestFit of the University of Wisconsin Genetics Computer Group[19] in the NBRF or GenBank data bases, respectively. A FASTDB search using the IntelliGenetics Suite PAM matrix search[20] was also performed.

cDNA Cloning and Nucleotide Sequence Analysis

A λgt11 library from human foreskin keratinocytes grown in 1.0 mM $Ca^{++}$ (Clontech) was screened with the ECS-1 mAb according to procedures described by Young & Davis[16,17], which references are specifically incorporated herein by reference for this purpose. DNA sequencing was performed by the dideoxynucleotide chain termination method[18] using Sequenase® (T7 DNA polymerase; United States Biochemical Co.). Double-stranded cDNA inserts in pGEM-3Z were sequenced in both orientations by using T7 and SP6 promoter primers and subsequently by synthetic 17-mer oligonucleotides made to previously sequenced regions. Analysis of hydropathy and secondary structure were carried out using the program PepPlot®.[19,21]

By application of techniques such as DNA mutagenesis, the present invention allows the ready preparation of so-called "second generation" molecules having modified or simplified protein structures. Second generation proteins will typically share one or more properties in common with the full-length ESA antigen, such as a particular antigenic/immunogenic epitopic core sequence. Epitopic sequences can be provided on relatively short molecules prepared from knowledge of the peptide, or underlying DNA sequence information. Such variant molecules may not only be derived from selected immunogenic/antigenic regions of the protein structure, but may additionally, or alternatively, include one or more functionally equivalent amino acids selected on the basis of similarities or even differences with respect to the native sequence.

Epitope Selection and Epitopic Core Sequences of the ESA Antigen

Immunopositive recombinant phage containing ESA cDNA (see FIG. 2 nucleotide sequence) inserts and λgt11 (2000 plaque-forming units) were separately used to infect *Escherichia coli* (Y1090) on petri dishes at 42° C. for 5 hours and induced for the expression of fusion protein.[22] The expressed bacterial proteins were adsorbed to nitrocellulose filters overnight and then rinsed in TBS (50 mM tris, pH 8.0, 150 mM NaCl) for 10 minutes at room temperature. Subsequent to blocking in 0.5% Triton X-100, 3% bovine serum albumin (BSA) in TBS for 15 minutes, the filters were incubated for 2 hours with the ECS-1 ascites diluted 1:100 in 0.5% Triton X-100, 3% BSA in TBS. Filters were washed three times with a solution of 0.5% Triton X-100 in TBS and antibody was separately eluted from each filter with three 1 minute washes in 1 ml 5 mM glycine-HCl (pH 2.3), 150 mM NaCl, 0.5% Triton X-100, BSA (100 μg/ml). The combined washes were immediately neutralized with tris-HCl, pH 7.4 to a final concentration of 50 mM. Each selected antibody was then used for IF staining of human skin sections.

It is proposed that particular advantages may be realized through the preparation of synthetic peptides which include epitopic/immunogenic core sequences. An epitope core sequence, as used herein, is a relatively short stretch of amino acids that is "complementary" to and therefore will bind, antigen binding sites on ESA-directed antibodies. Additionally or alternatively, an epitopic core sequence is one that will elicit antibodies that are cross-reactive with ESA-directed antibodies. It will be understood that in the context of the present disclosure, the terms "complementary" refers to amino acids or peptides that exhibit an attractive force towards each other. Thus, certain epitope core sequences of the present invention may be operationally defined interns of their ability to compete with or perhaps displace the binding of the desired ESA antigen with the corresponding OMP-directed antisera.

In general, the size of the polypeptide antigen is not believed to be particularly crucial, so long as it is at least large enough to carry the identified core sequence or sequences. The smallest useful core sequence anticipated by the present disclosure would be on the order or about six amino acids in length. Thus, this size will generally correspond to the smallest peptide antigens prepared in accordance with the invention. However, the size of the antigen may be larger where desired, so long as it contains a basic epitopic core sequence.

Accordingly, through the use of computerized peptide sequence analysis program (DNAStar Software, DNAStar, Inc., Madison, Wisc.), the inventors propose to identify additional peptidyl regions of the ESA antigen that are believed to constitute epitopic core sequences comprising particular epitopes of the protein.

Synthesis of epitopic sequences, or peptides which include an antigenic epitope within their sequence, are readily achieved using conventional synthetic techniques such as the solid phase method (e.g., through the use of commercially available peptide synthesizer such as an Applied Biosystems Model 430A Peptide Synthesizer). Peptide antigens synthesized in this manner may then be aliquoted in predetermined amounts and stored in conventional manners, such as in aqueous solutions or, even more preferably, in a powder or lyophilized state pending use.

In general, due to the relative stability of peptides, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include gents including buffers such as Tris or phosphate buffers to maintain a pH of 7.0 to 7.5. Moreover, it may be desirable to include agents which will inhibit microbial growth, such as sodium azide or Merthiolate. For extended storage in an aqueous state it will be desirable to store the solutions at 4° C., or more preferably, frozen. Of course, where the peptide(s) are stored in a lyophilized or powdered state, they may be stored virtually indefinitely, e.g., in metered aliquots that may be rehydrated with a predetermined amount of water (preferably distilled or buffer prior to use.

Indirect Immunofluorescence

Double indirect immunofluorescent staining was performed on cryostat sections of human skin with the ECS-1 mAb as previously described.[13] Briefly, epidermal cells were rinsed in 0.01M phosphate-buffered saline (PBS) and subsequently incubated in 0.01M PBS, pH 7.3, containing ECS-1 mAb diluted 1:100 in 0.01M PBS at room temperature for 30 minutes. The sections were then washed in 0.01M PBS for 15 minutes and exposed to FITC-conjugated affinity purified goat anti-mouse IgM (Jackson Immunoresearch Laboratories, West Grove, Pa.) at room temperature for 30 minutes. Following a 15 minute wash in PBS, pH 7.4, the cells were examined by fluorescent microscopy.

In Situ Hybridization

Sense and antisense $^{35}$S-labeled riboprobes for in situ hybridization were synthesized from the SP6 and T7 promoters of pESA2.0 cDNA in pGEM-3Z using the Riboprobe Gemini System (Promega) according to the manufacturer's recommendations and equal amounts hybridized to cryostat sections of normal skin according to the protocol of Harper and Marselle.[23] Sense probes were transcribed from the SP6 promoter of NdeI linearized pESA2.0 while antisense probes were transcribed from the T7 promoter of KpnI linearized pESA2.0. Following hybridization, sections were treated with a solution of RNase A and RNase T1 to remove unhybridized probe, autoradiographed in Kodak NTB2 nuclear track emulsion, and exposed at 4° C. for 4 days. Sections were counter-stained in hematoxylin and eosin for analysis.

Northern Blot Analysis

Total cellular RNA was isolated from tissues or cell culture lines in guanidine isothiocyanate and purified by cesium chloride gradient centrifugation as described.[24] Thirty μg of total cellular RNA was electrophoresed in formaldehyde gels, transferred to nitrocellulose (S&S), and hybridized with oligolabeled $^{32}$P-ESA cDNA by routine methods.[25]

Southern Blot Analysis

Human genomic DNA and genomic DNA from nonhuman species were isolated, digested, separated by electrophoresis in 1% agarose gels, transferred to Zetaprobe membranes (Bio-Rad), and hybridized in 5× SSC (1× SSC= 0.15M NaCl, 0.015M NaCitrate, pH 7.0), 1% SDS, 20 mM $NaPO_4$, 100 μg/ml herring sperm DNA, 250 mg/ml powdered milk, and 40% formamide overnight at 42° C.[26] The filters were subsequently washed in 0.1× SSC, 0.1% SDS at room temperature, then in 0.1× SSC, 0.1% SDS at 55° C. and exposed at −70° C. for 10 days. Additionally, filters were hybridized under low stringency conditions in 5× SSC, 5× Denhardt's solution, 100 μg/ml herring sperm DNA, 1% sodium pyrophosphate, 0.1% SDS, 10% dextran sulfate, 43% formamide at 37° C., washed in 6× SSC, 0.1% SDS at room temperature, then in 2× SSC, 0.1% SDS at 30° C. and exposed at −70° C. for 3–10 days.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

CLONING AND CHARACTERIZATION OF cDNA CLONES FOR ESA ANTIGEN

The present example demonstrates the cloning and characterization of cDNA clones that encode the 41.5 kDa epidermal surface antigen of the present invention. The sequence encoded by the cDNA clone is depicted at FIG. 1 (SEQ ID NO:2).

A λt11 expression library made from poly(A)-selected RNA from human keratinocytes grown in 1 mM $Ca^{++}$ was purchased from Clontech Laboratories (Palo Alto, Calif.). To identify cDNAs encoding the ECS-1 antigen, approximately $2\times10^6$ recombinant phage plaques were screened in duplicate with the ECS-1 monoclonal IgM antibody.[16,17] The following three rounds of plaque purification and immunoscreening, four independent plaques remained immunoreactive. Using the insert from one phage, λ25-1B, as probe, positive hybridization to mini-DNA preparations from each of the four positive plaques digested with Eco RI to release cDNA inserts[25,26], demonstrated that the independently isolated phage contained identical or overlapping DNA sequences. Three of the fourth positive phage contained DNA inserts of 2.0 kb, while a fourth, λ14-1B, contained a slightly larger cDNA of 2.487 kb. Inserts from λ25-1B and λ14-1B were subcloned into pGEM-3Z vector (Promega) and subsequently named pESA2.0 and pESA2.5, respectively.

To verify that proteins encoded for by λ25-1B and λ14-1B bound ECS-1 mAb, an epitope selection was used to affinity purify the ECS-1 mAb with λ25-1B and λ14-1B fusion proteins.[22] The λ25-1B and λ14-1B epitope-selected antibody preparations, but not preparations selected by λgt11 alone, were then shown by IF to bind the epidermis in frozen skin sections in a manner identical to that of ECS-1 which had not been epitope-selected (see FIG. 3A).

DNA sequence analysis of pESA2.0 and pESA2.5 revealed that pESA2.0 was a partial cDNA which was contained within the full-length pESA2.5 cDNA. The composite nucleotide and corresponding deduced amino acid sequences of the pESA2.5 clone are shown in FIG. 1. Sequence analysis of the full-length ESA cDNA revealed an open reading frame of 1137 bases that begins with the penultimate A codon at the 5' terminus of the codon ACG (threonine), and encodes a polypeptide of 379 amino acids. The 5' end of the cDNA consisted of an untranslated region of 126 base pairs with a 1.488 kb 3' untranslated region. A consensus polyadenylation signal (AATAAA) was located at position 2466. The nucleotide sequence GXXGXXAXX-ATG (SEQ id no:3), surrounding the first in-frame ATG beginning at base 127, agreed with the consensus sequence for initiation of protein translation.[27] Therefore, the first amino acid was assigned to this codon.

The predicted molecular weight of the deduced ESA polypeptide is 41.5 kDa. This molecular weight approximates the 35 kDa protein detected by Western blotting epidermal extracts with the ECS-1 mAb.[13] Analysis of the polypeptide sequence, indicates that the ESA protein does not contain a signal peptide, transmembrane region, nor sites for N-glycosylation. Exhaustive comparison of the cDNA and deduced protein sequences with the GenBank and NBRF-protein data bases[19], respectively, and a search with FASTDB of the IntelliGenetics Suite PAM matrix[20] revealed no significant sequence homology with any known gene or protein. Thus, the ESA cDNA represents a previously uncharacterized epidermal protein.

Figure 3B:
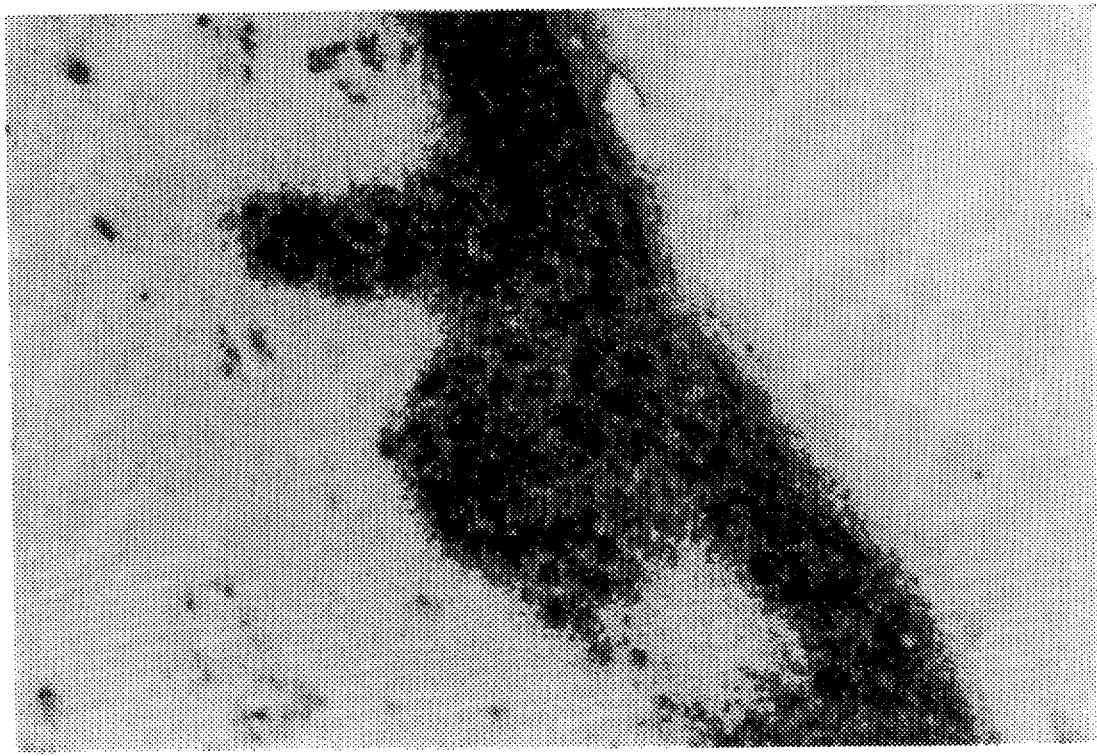

Predictions of hydrophilicity, secondary structure, and antigenicity of the deduced ESA protein sequence[19,21] were plotted by computer analysis. Several regions of antigenicity and high surface probability have been found within the ESA protein (FIG. 3B). Hydropathy analysis of the ESA polypeptide indicates that the amino terminus is composed of a hydrophobic region of 100 amino acids followed by a hydrophilic region of 190 amino acids. The hydrophilic WP terminus has a high antigen index and surface probability. Therefore, these two regions may represent two distinct domains of the ESA protein.

Exhaustive searches of DNA and protein sequence databases revealed only extremely low levels of homology between ESA and any of the known protein and DNA sequences, including those of adhesion molecules. Furthermore, examination of the ESA sequence for known motifs, such as those for binding to calcium or GTP, does not provide any information pertaining to the possible function of this protein. Therefore, the ESA antigen presents a novel, yet highly phylogenetically conserved protein never before identified.

Localization of ESA mRNA by In Situ Hybridization

Figure 4A:
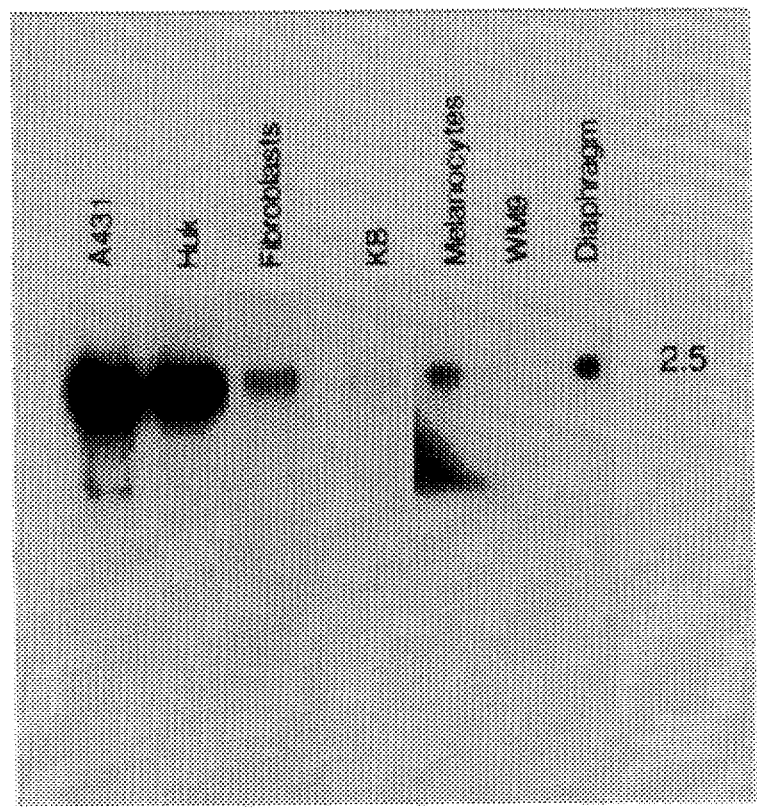
FIG. 4A and FIG. 4B—Tissue and cell-type specificity of ESA expression as seen from Northern blot analysis of total RNA (30 µg per lane). RNAs from human squamous cell carcinoma line A431 (lane 1), cultured human foreskin keratinocytes (lane 2), cultured human fibroblasts (lane 3), human squamous cell carcinoma line KB (lane 4), cultured human melanocytes (lane 5), human melanoma cell line WM9 (lane 6), and human diaphragm (lane 7). Same RNAs probed with human GAPDH cDNA to show relative amounts of RNA in each lane.
Figure 5:
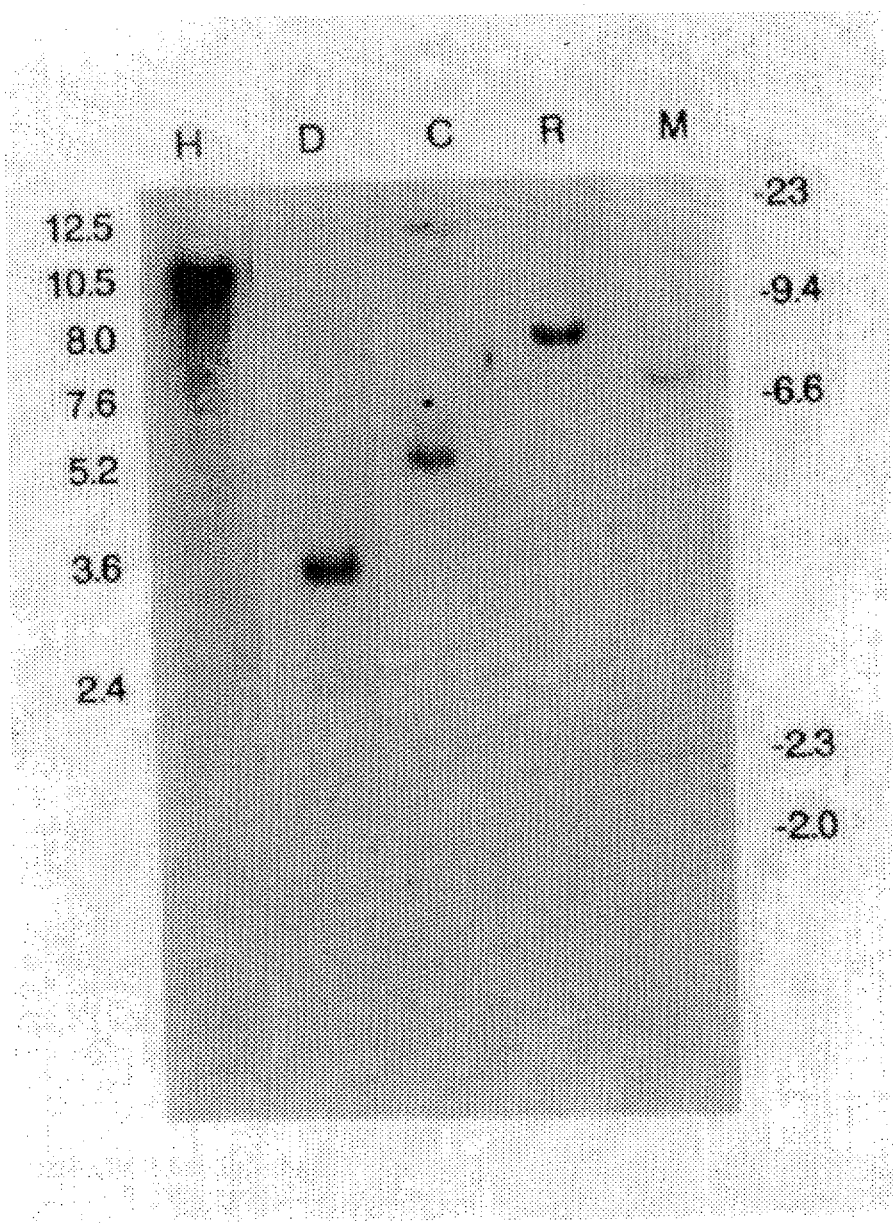
FIG. 5—Conservation of the ESA gene during evolution is demonstrated by probing genomic DNA from human (lane 1), dog (lane 2), cat (lane 3), rabbit (lane 4), and mouse (lane 5) with the ESA cDNA. Sizes of hybridizing bands are indicated on the left. The position of molecular weight markers are shown on the right.

It was previously reported that indirect immunofluorescent staining of human skin sections with the ECS-1 mAb resulted in intercellular staining of the nucleated layers of the epidermis with increasing fluorescent intensity from the basal to suprabasal layers.[13] To examine the correlation between mRNA and protein expression for ESA, the technique of in situ hybridization[23] was employed. As shown in FIG. 4A, indirect immunofluorescent staining of human epidermis with the ECS-1 mAb demonstrates staining of the nucleated layers of the epidermis with the exception of the basal cells. Cryostat sections of human epidermis were hybridized with radiolabeled cRNA probes transcribed from the Sp5 and T7 promoters of the pESA2.0 cDNA, corresponding to antisense or sense probes, respectively, for the mRNA encoding ESA. A section hybridized with the antisense ESA probe is shown in FIG. 3B. When antisense $^{35}$S-UTP-labeled cRNA probes complementary to ESA mRNA were hybridized with skin sections, abundant grains were localized throughout the epidermis, including the most basal cell layer. Hybridization was significantly lower, although not completely absent in the dermis. This may be due to the presence of low amounts of ESA transcripts in dermal fibroblasts (FIG. 5), however, the dermis remained negative for expression of ESA protein (FIG. 3A).

The presence of ESA mRNA transcripts in areas negative for expression of ESA protein, may be due to post-transcriptional regulation, either at the level of mRNA translation or post-translation processing, which would prevent the generation of stable ESA protein in these mRNA positive cells. Epidermal sections hybridized with the sense $^{35}$S-UTP-labeled cRNA probe displayed only background levels of hybridization which could only be detected under high magnification.

RNA Expression Analysis

To determine the size of the ESA mRNA, and to analyze the tissue specificity of ESA gene expression, total RNA isolated from several different cell types was examined by Northern blot analysis for the presence of ESA transcripts. As shown in FIG. 5A, hybridization of the pESA2.5 cDNA to RNA from cultured keratinocytes, melanocytes, fibroblasts, several malignant cell lines derived from epidermal tissue, and diaphragm identified a 2.5 kb ESA transcript. Based on this size estimate, the 2.487 clone encompassed 100% of the corresponding mRNA. Although the 2.5 kb ESA transcript was detectable in fibroblasts and diaphragm, the level of ESA mRNA expression in these tissues was much lower than that seen in the epidermis and in cultured cells normally found in the epidermis. Additionally, muscle tissue stained with ECS-1 mAb demonstrated the absence of ESA protein in this tissue. ESA mRNA may be constitutively expressed at low levels in some nonepidermal tissues, with high levels of transcription occurring in the epidermis. No transcripts were detected in total RNA from human hemopoietic cells. Relative quantities of RNA from each sample were visualized by probing with a ubiquitously expressed human GAPDH cDNA[28] (FIG. 5B).

EXAMPLE 2

BIOLOGICALLY FUNCTIONAL EQUIVALENT AMINO ACIDS

The amino acid sequence (FIG. 1) and the corresponding nucleic acid sequence (FIG. 2) of the ESA antigen of the present invention has been determined. However, it will be understood by those of skill in the art that numerous modifications and changes may be made in the structure of the desired ESA antigen, or sub-portions thereof, and still obtain a molecule having like or otherwise desirable characteristics.

It is known, for example, that certain amino acids may be substituted for other amino acids in a protein structure without appreciable loss of interactive binding capacity with structures such as, for example, binding sites on other molecules, including in the present case, epithelial cell proteins and extracellular matrix proteins. Since it is the interactive capacity and nature of a protein that defines that protein's biological functional activity, certain amino acid sequence substitutions can be made in a protein sequence (or, of course, its underlying DNA coding sequence) and nevertheless obtain a protein with like or even counterveiling properties (e.g., antagonistic v. agonistic). It is thus contemplated by the inventors that various changes may be made in ESA protein, peptide, or underlying DNA sequences without appreciable loss of their biological utility or activity.

In making such changes, the hydropathic index of amino acids may be considered. The importance of the hydropathic amino acid index in conferring interactive biologic function on a protein is generally understood in the art (Kyte & Doolittle, J. Mol. Biol., 157:105–132, 1982). It is known that certain amino acids may be substituted for other amino acids having a similar hydropathic index or score and still result in a protein with similar biological activity. Each amino acid has been assigned a hydropathic index on the basis of their hydrophobicity and charge characteristics, as displayed below in Table I.

TABLE I

| Amino Acids | Hydropathic Index |
|---|---|
| Isoleucine | 4.5 |
| Valine | 4.2 |
| Leucine | 3.8 |
| Phenylalanine | 2.8 |
| Cysteine/cystine | 2.5 |
| Methionine | 1.9 |
| Alanine | 1.8 |
| Glycine | −0.4 |
| Threonine | −0.7 |
| Tryptophan | −0.9 |
| Serine | −0.8 |
| Tyrosine | −1.3 |
| Proline | −1.6 |
| Histidine | −3.2 |
| Glutamic Acid | −3.5 |
| Glutamine | −3.5 |
| Aspartic Acid | −3.5 |
| Asparagine | −3.5 |
| Lysine | −3.9 |
| Arginine | −4.5 |

It is believed that the relative hydropathic character of the amino acid determines the secondary structure of the resultant protein, which in turn defines the interaction of the protein with other molecules, for example, intra- or extra-cellular or transmembrane epithelial proteins, adhesion proteins, or various other enzymes, substrates, receptors, hormones, antibodies, antigens, and the like. It is known that an amino acid may be substituted by another amino acid having a similar hydropathic index and still obtain a biological functionally equivalent protein. In such changes, the substitution of amino acids whose hydropathic indices are within ±2 is preferred, those which are within ±1 are particularly preferred, and those within ±0.5 are even more particularly preferred.

Substitution of like amino acids can also be made on the basis of hydrophilicity, particularly where the biological functional equivalent protein or peptide thereby created is intended for use in immunological embodiments. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein.

As detailed in U.S. Pat. No. 4,554,101, the following hydrophilicity values have been assigned to amino acid residues as detailed below:

TABLE II

| Amino Acids | Hydrophilicity Value |
|---|---|
| arginine | +3.0 |
| lysine | +3.0 |
| aspartate | +3.0±1 |
| glutamate | +3.0±1 |
| serine | +0.3 |
| asparagine | +0.2 |
| glutamine | +0.2 |
| glycine | 0 |
| proline | −0.5±1 |
| threonine | −0.4 |
| alanine | −0.5 |
| histidine | −0.5 |
| cysteine | −1.0 |
| methionine | −1.3 |
| valine | −1.5 |
| leucine | −1.8 |

TABLE II-continued

| Amino Acids | Hydrophilicity Value |
|---|---|
| isoleucine | −1.8 |
| tyrosine | −2.3 |
| phenylalanine | −2.5 |
| tryptophan | −3.4 |

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally based on the relatively similarity of R-group substituents, for example, in terms of size, electrophilic character, charge, and the like. In general, preferred substitutions which take various of the foregoing characteristics into consideration are well known to those of skill in the art and include those outlined in Table III.

TABLE III

| Original Residue | Exemplary Substitutions |
|---|---|
| Ala | gly; ser |
| Arg | lys |
| Asn | gln; his |
| Asp | glu |
| Cys | ser |
| Gln | asn |
| Glu | asp |
| Gly | ala |
| His | asn; gln |
| Ile | leu; val |
| Leu | ile; val |
| Lys | arg; gln; glu |
| Met | leu; ala |
| Ser | thr |
| Thr | ser |
| Trp | tyr |
| Tyr | trp; phe |
| Val | ile; leu |

EXAMPLE 3

HOST CELL CULTURES AND VECTORS OF ESA ANTIGEN

In general, of course, prokaryotes are preferred for the initial cloning of DNA sequences and constructing the vectors useful in the invention. For example, E. coli strain LE392 is particularly useful. Other microbial strains which may be used include E. coli strains such as E. coli LE392, E. coli B, and E. coli X 1776 (ATCC No. 31537). These examples are, of course, intended to be illustrative rather than limiting.

Prokaryotes are also preferred for expression. The aforementioned strains, as well as E. coli W3110 (F-, lambda-, prototrophic, ATCC No. 273325), bacilli such as Bacillus subtilis, or other enterobacteriaceae such as Salmonella typhimurium or Serratia marcesans, and various Pseudomonas species may be used.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example E. coli is typically transformed using pBR322, a plasmid derived from an E. coli species (Bolivar et al., (1977) Gene, 2:95). pBR322 contains genes for ampicillin and tetracycline resistance and thus provides easy means for identifying transformed cells. The pBluescript plasmid, or other microbial plasmid or phage must also contain, or be modified to contain, promoters which can be used by the microbial organism for expression of its own proteins.

In addition, phage vectors containing replicon and control sequences that are compatible with the host microorganism can be used as a transforming vector in connection with these hosts. For example, the phage lambda GEM™-11 may be utilized in making recombinant phage vector which can be used to transform host cells, such as E. coli LE392.

Those promoters most commonly used in recombinant DNA constructions include the B-Lactamase (penicillinase) and lactose promoter systems (Chang et al. (1978) Nature, 375:615; Itakura et al. (1977) Science 198:1056; Goeddel et al., (1979) Nucleic Acids Res., 8:4057) and a tryptophan (trp) promoter system (Goeddel et al., (1980) Nucleic Acids Res., 8:4057); EPO Appl. Publ. No. 0036776). While these are the most commonly used, other microbial promoters have been discovered and utilized, and details concerning their nucleotide sequences have been published, enabling a skilled worker to ligate them functionally with plasmid vectors (EPO Appl. Publ. No. 0036776).

In addition to prokaryotes, eukaryotic microbes, such as yeast cultures may also be used. Saccharomyces cerevisiae, or common baker's yeast is the most commonly used among eukaryotic microorganisms, although a number of other strains are commonly available. For expression in Saccharomyces, the plasmid YRp7, for example, is commonly used (Stinchcomb et al., (1979) Nature, 282:39; Kingsman et al., (1979) Gene, 7:141; Tschemper et al., 1980; Gene, 10:157). This plasmid already contains the trp1 gene which provides a selection marker for a mutant strain of yeast lacking the ability to grow in tryptophan, for example ATCC No. 44076 or PEP4-1 (Jones, (1977) Genetics, 85:12). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., (1980) J. Biol. Chem., 255:2073) or other glycolytic enzymes (Hess et al., (1968) J. Adv. Enzyme Reg., 7:149; Holland et al., (1978) J. Biol. Chem. 225:2073), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions are the promoter region for alcohol dehydrogenase 2, isocytochrome C. acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture (esp. Baculovirus, insect cells). However, interest has been greatest in vertebrate cells, and propagation of vertebrate cells in culture (tissue culture) has become a routine procedure in recent years (*Tissue Culture*, 1973; Academic Press, Kruse and Patterson, editors). Examples of such useful host cell lines are VERO and HeLa cells, Chinese hamster ovary (CHO) cell lines, and W138, BHK, COS-7, 293 and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication (Fiers et al., 1978; Nature, 273:113). Smaller or larger SV40 fragments may also be used, provided there is included the approximately 350 bp sequence extending from the Hind III site toward the Bgl I site located in the viral origin of replication. Further, it is also possible, and often desirable, to utilize promoter or control sequences normally associated with the desired gene sequence, provided such control sequences are compatible with the host cell systems.

As origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

EXAMPLE 4

CHARACTERIZATION OF PHYLOGENETIC CONSERVATION OF THE ESA GENE

The present example provides a comparison of genomic DNA from a number of animal species, and demonstrates that the ESA gene is conserved throughout mammalian evolution.

Comparison of conserved regions between human and mouse will be used to make blocking antibodies, whereas areas of differences will be used to generate species specific antibodies.

Figure 4B:
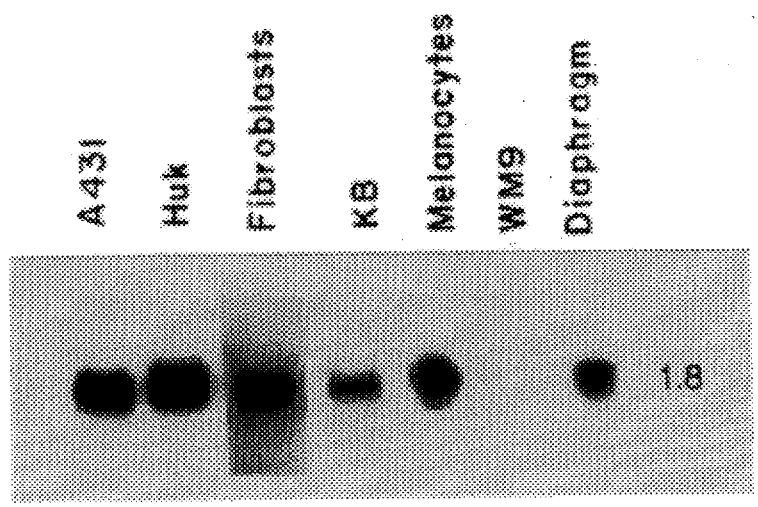

Hybridization of genomic DNA from dog, cat, rabbit, and mouse with the ESA cDNA under moderately stringent conditions reveals that in each of these species there are sequences which are homologous to the ESA cDNA (FIG. 4). However, hybridization to genomic DNA from Xenopus and Drosophila, even under low stringency conditions, demonstrate the absence of homologous sequences in these species. Furthermore, in IF experiments, the present inventors have found that the ECS-1 mAb stains epidermis from rabbit and mouse as well as humans. The results support the proposition that the ESA protein, or at least the epitope recognized by ECS-1, is also conserved. These studies establish that the ESA gene and protein are conserved throughout mammalian evolution. The ESA gene product may also be critical for normal epidermal development and/or function.

EXAMPLE 5

MOUSE ESA

Using the Lambda Zap library containing newborn mouse cDNA, the mouse ESA cDNA was cloned using the human ESA 2.0 EcoRI cDNA fragment isolated as described herein by the inventors.

1. SCREENING: 20 NZCYM plates×$10^6$ plaques=20,000,000 plaques. To 800 µl of BB4 host cells ($OD_{600}$=0.5 cells/ml).

The phage were added and allowed to adhere for 30 minutes. 6.5 ml of NZCYM top agarose was then added. This was then poured over the large NZCYM plates. These were then incubated overnight at 37° C., were chilled at 4° C. for two hours, and the DNA transferred to nitrocellulose membranes. Once transferred, the DNA was denatured, neutralized, and rinsed. The filters were air-dried and then baked at 80° C. for two hours.

2. PROBING

The filters were prehybridized in:

50% deionized formamide

5× SSC

1× PE

20 µg/ml ssDNA overnight at 50° C.

The probe was labeled as follows:

2 µl human ESA 2.0 EcoRI cDNA fragment

1 µl random hexamers

10 µl 12.5× reaction buffer

1 µl 10 mg/ml BSA

5 µl $^{32}$P-dCTP (50 uCi)

1 µl Klenow

5 µl $H_2O$ incubated at 37° C. for 30 minutes and then purified over a spin column.

The filters were hybridized with this probe in the hybridization buffer (same as prehyb. buffer but replaced with fresh) overnight at 50° C. The filters were washed twice in 2× SSC/0.1% SDS at room temperature then twice in 0.1× SSC/0.1% SDS at 55° C. The filters were then autoradiographed at −70° C. overnight.

| 3. RESULTS: | First screening | - 6 positive with duplicates<br>2 positive /no duplicates<br>Lysate #'s 244–254 taken<br>11 lysates total |
|---|---|---|

Next screen—positive with duplicates for all except plate #9 (lys #252). New lysates 262–271 (with 264B which was positive. 11 lysates total Next screen—Lysates Purified all except #'s 262 and 263. New lysate #'s 274P-282P with lysates 272 and 273 taken from 262 263, respectively.

Phage Prep on these eight lysates (none done on 282P as it was a duplicate of 281P):

| Lysate # | Concentration | Amount |
| --- | --- | --- |
| 274P | 0.36 µg/ml | 36 µg |
| 275P | 0.70 µg/ml | 70 µg |
| 276P | 0.20 µg/ml | 20 µg |
| 277P | 0.42 µg/ml | 42 µg |
| 278P | 0.12 µg/ml | 12 µg |
| 279P | 0.13 µg/ml | 13 µg |
| 280P | 0.30 µg/ml | 30 µg |
| 281P | 0.40 µg/ml | 40 µg |

These lysates are stored in 100 µl TE buffer at 4° C.

4. Analyzing the phage prep results:

2 µg of each phage prep was digested with XbaI, EcoRI, some with XhoI/NotI, and some with XhoI/XbaI.

5. A Southern blot of these digestions was performed. A 680 bp band hybridized to the 2.0 bp ESA insert. The phage were converted to pBluescript.

RESULTS: Hybridization of the Southern from #4 (above) to the 2.0 Kb EcoRI fragment from pESA2000 revealed a band at about 680 bp that hybridizes to the ESA 2.0 probe. It has a high degree of homology 65% to the 3' ESA human sequences.

6. Excision was performed following the protocol provided for lambdaZAP by Stratagene.

RESULTS: Many colonies from all three original lysate stocks 275, 277, 280.

7. STET-Miniprep and subsequent electrophoresis performed on colonies from the three clones showed that the pBluescript SK-plasmid was there.

8. Magic Miniprep from glycerol stocks of the three clones results:

275-0.13 µg/µl—39 µg total—Plasmid #p385 Plasmid Name: pESAmI

277—nothing

280-0.05 µg/µl—15 µg total—Plasmid #p386 Plasmid Name: pESAmII

To reduce the volume, the DNA was extracted with phenol/chloroform and EtOH-precipitated. The DNA was redissolved in TE to the concentrations: p385—2 µg/µl and p386—1 µg/µl.

9. p385 was digested with EcoRI to excise the 680 bp band and for Southern hybridization to the 2.0 Kb ESA probe. The 680 bp band was Genecleaned and did hybridized to the probe. 10 µg of p385 were further analyzed to confirm the map locus. SK primer $T_3$ and $T_t$ for automated sequencing demonstrated that the mouse ESA clone is 60% homologous to the 3' end of the human ESA cDNA.

10. The lambdaZAP library was rescreened with the 680 bp clone. 20 plates at $7.8 \times 10^5$ plaques=15,600,000 plaques. Results are as follows:

First screen: Five positive with duplicates. Lysate numbers 282–286.

Second Screen: Many positive duplicates for all five previous clones. These cells contained a 680 bp insert.

The third screen is currently being done from plates where the plaques are well separated for purification. Eco R1 shows a 680 bp fragment in 3 clones, plus an 800 bp band in one. The library will be rescreened with a 400 bp 5' ESA cDNA sequence.

The 680 bp cDNA mouse clone maps to mouse chromosome 11 in the same exact region as the human ESA clone mapped. Therefore part of the mouse ESA cDNA has been cloned. The library will be rescreened and additional clones to sequence will be obtained.

The mouse RNA Northern analysis demonstrated 02.4 kb ESA RNA on Norther blotting.

PROPHETIC EXAMPLE 6

PROPOSED USES OF NUCLEIC ACID SEQUENCES

The DNA sequence information provided by the present disclosure allows for the preparation of relatively short DNA (or RNA) sequences having the ability to specifically hybridize to gene sequences of the selected ESA antigen gene. In these aspects, nucleic acid probes of an appropriate length are prepared based on a consideration of the natural sequence or derived from flanking regions of the ESA gene, such as regions downstream of the gene as found in plasmid pESA2.0 or plasmid pESA2.5. The ability of such nucleic acid probes to specifically hybridize to ESA gene sequences lend them particular utility in a variety of embodiments. Most importantly, the probes can be used in a variety of diagnostic assays for detecting the presence of the ESA antigen encoded thereby in a given sample. However, other uses are envisioned, including the use of the sequence information for the preparation of mutuant species primers, or primers for use in preparing other genetic constructions.

To provide certain of the advantages in accordance with the invention, the preferred nucleic acid sequence employed for hybridization studies or assays includes sequences that are complementary to at least a 10 to 20, or so, nucleotide stretch of the sequence. A size of at least 10 nucleotides in length helps to ensure that the fragment will be of sufficient length to form a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained. Thus, one will generally prefer to design nucleic acid molecules having ESA gene-complementary stretches of 15 to 20 nucleotides, or even longer where desired. Such fragments may be readily prepared by, for example, directly synthesizing the fragment by chemical means, by application of nucleic acid reproduction technology, such as the PCR technology of U.S. Pat. No. 4,603,102, or by introducing selected sequences into recombinant vectors for recombinant production.

The nucleotide sequences of the invention are important for their ability to selectively form duplex molecules with complementary stretches of the corresponding ESA gene. Depending on the application envisioned, one will desire to employ varying conditions of hybridization to achieve varying degrees of selectivity of the probe toward the target sequence. For applications requiring a high degree of selectivity, one will typically desire to employ relatively stringent conditions to form the hybrids, for example, one will select relatively low salt and/or high temperature conditions, such as provided by 0.02M–0.15M NaCl at temperatures of 50° C. to 70° C. These conditions are particularly selective, and tolerate little, if any, mismatch between the probe and the template or target strand.

Of course, for some applications, for example, where one desires to prepare mutants employing a mutant primer strand hybridized to an underlying template, less stringent hybridization conditions are called for in order to allow formation of the heteroduplex. In these circumstances, one would desire to employ conditions such as 0.15M–0.9M salt, at temperatures ranging from 20° C. to 55° C. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

EXAMPLE 7

ANTI-ESA ANTIBODIES

The present example is provided to outline the particular method that was used by the present inventors to prepare the anti-ESA antibodies of the present invention. However, other methods effective for the preparation of an antibody specific for the ESA antigen having an amino acid sequence of SEQ ID NO:1, or a nucleotide sequence of SEQ ID NO:2, or a fragment thereof, may also be employed in the practice of the present invention.

The antibodies of the present example are polyclonal antibodies. The present example is submitted to satisfy best mode requirements.

PREPARATION OF IMMUMOGENS

Several antigens, and therefore several polyclonal antibodies, have been prepared by the present inventors.

Peptides corresponding to amino acid residues 193–207 and 277–291 were synthesized (Analytical Chemistry Department UTHSCH). Three (3) mg hemocyanin and 10 mg. of each peptide were then dissolved in a total volume of 0.9 ml. PBS. After the addition of 0.5% glutaraldehyde, the mixture was incubated overnight at room temperature and diluted to a total volume of 3 ml. with PBS.

Initial immunization of New Zealand white rabbits was performed with complete Freund's adjuvant containing 250 µg of immunogen, 250 µl PBS, and 500 µl complete Freund's adjuvant. Each rabbit was injected subcutaneously on the back at several sites, 100 µl of the immunogen-containing solution at each site. One month after the initial injection, the animals were boosted with incomplete Freund's adjuvant containing the respective peptide. Two weeks after the boost, the rabbits were bled from the ear vein, the serum from the blood separated, and the anti-ESA antibody titer level of the serum determined. The boosting of the rabbits with Freund's adjuvant is to be continued at monthly intervals, and the animals will be bled at two week intervals after each monthly boost.

The antigens used as immunogens in the present example also include B-galactosidase-ESA fusion proteins that correspond to fragments of the 379 a.a. ESA peptide of SEQ ID NO:1. An antigen encoded by amino acids 1–238 of the sequence was employed as an immunogen. This antigen is designated for purposes of the present example as the 841 NH₃ peptide, as the sequence corresponds to a segment obtained from the NH₃ terminal of the complete peptide. The antigen encoded by amino acids 240–291 of SEQ ID NO:1 was also employed as an immunogen, and is designated for purposes of the present example as the 359 COOH peptide, as the sequence corresponds to a segment obtained from the COOH terminal of the peptide. In addition, a fusion protein corresponding to the entire 291 a.a. ESA antigen was prepared and used as immunogen. Each of these designated antigens were expressed in *E. coli* using a pEX vector (Boeringer Mannaheim) and affinity purified (affinity column with an anti-β galactosidase antibody, antigen eluted with glycine, low pH buffer. The affinity purified antibody was then put in 500 µl complete Freud's adjuvant, 250 µl PBS, and 250 µl of β-galactosidase-affinity purified fusion peptide. After an initial injection of Freund's complete adjuvant (as indicated), the animals were given monthly booster injections of the 841 NH₃ peptide or the 359 COOH peptide in an incomplete Freund's adjuvant. Serum was collected from the rabbits by ear vein bleeding, the serum separated, and the anti-ESA antibody titer of the serum determined.

All of the above described antigens were injected at an initial dose of 250 µg ESA antigen contained in 1 ml. of a carrier solution after the initial injection of the animal with Freund's complete adjuvant.

The carrier solution used for the subsequent booster injections of the immunogen, per ml, was made up of:

500 µl incomplete Freund's Adjuvant

250 µl PBS

250 µl of peptide linked to keyhole limpet hemocyanin (Cal Biochem)

All animals were bled at 2 week intervals after each booster treatment to determine the titer of anti-ESA antibody in the animal serum. All serum samples prepared from blood collected from immunized animals were assayed to determine the anti-ESA antibody titer level. The method for assay of antibody titer level in a serum sample is well known to those of skill in the art. The target anti-ESA antibody titer level used was a 1:64,000 dilution, sufficient to give detection of the ESA protein by Western Blotting. The technique for Western Blotting is well known to those of skill in the art.

PROPHETIC EXAMPLE 8

PROPOSED CLINICAL USE OF ESA cDNA FOR DETECTION OF CHROMOSOME 17 ABNORMALITIES

The present example is provided to demonstrate anticipated potential uses for the disclosed ESA cDNA. For example, the ESA cDNA may be used as a genetic marker for NF1 in families, as well as a genetic marker for chromosome 17 between NF1 and the centromere of chromosome 17. The cDNA, or a fragment thereof, may be employed as a marker for linking studies to determine the linkage of ESA gene to genetic diseases, particularly those characterized by abnormal cell adhesion or by abnormal ESA protein.

According to one method of the ESA gene linkage studies, genomic DNA (rDNA) will be digested to completion with a restriction enzyme (such as Pst 1 enzyme), run on agarose gel, blotted to membrane, and hybridized to an ESA probe corresponding to SEQ ID NO:2.

Patients with an ESA gene abnormality are anticipated to be homozygous, heterozygous, or to have normal fragments or deleted fragments of the ESA gene depicted at SEQ ID NO:2. However, point mutations are not anticipated to be detectable through use of a RFLP analysis of the ESA gene.

Preparation and use of PCR polymorphisms and CA repeats will be developed for better probes for the ESA locus. Areas of high genetic variability among individuals may be found near or within the ESA locus which can be detected through comparison of an amplified DNA fragment.

Linkage Studies

YAC clones with chromosome 17 will be isolated in order to develop CA repeats for the 17 11q12 locus.

Somatic cell hybrids, cell lines, and YACs.

DCR-1 and NF13 are human-mouse somatic cell hybrids carrying human derivative chromosomes from two unrelated NF1 patients with translocation breakpoints within the NF1 gene. DCR-1 has a derivative chromosome 1 (1qter-p34.311 17q11-qter; Schmidt et al. (1987); Am. J. Med. Genet., 28:771–777; Menon et al. (1989); Genomics, 5:245–249)

and NF13 a derivative chromosome 22 (22qter-22q1111 17q112-17qter; Ledbetter et al. (1989); Am. J. Hum. Genet., 44:20–24)). The NF13 breakpoint maps approximately 60 kb q-distal to the DCR-1 breakpoint (O'Connell et al. (1990); Am. J. Hum Genet., 44:51–57). The SP3-10 hybrid contains a human derivative chromosome 15 (15qter-q2211 17q11-17qter; Sheer et al. 1983, 1985). MH22.6 carries an intact chromosome 17 as its only human genomic component (van Tuinen et al. (1987); Genomics, 1:374–381). The LMTk-mouse cell line was the fusion recipient for construction of DCR-1. NF13 and MH22.6 (van Tuinen et al. (1987) id.). Cell lines were obtained from the American Type Culture Collection (Rockville, Md.). UWA 106.3 is an immortalized lymphoblastoid cell line from an NF1 patient with an extensive detection encompassing the entire NF1 paternal allele and four flanking loci including D17S120, D17S115, D17S57, and D17S73. The three overlapping yeast artificial chromosome (YAC) clones A43A9.D8F4 and A113D7 form a contig that spans the NF1 gene (Marchuk et al. (1992); Genomics, 13:672–680).

For detection of restriction fragment length polymorphisms (RFLPs), cloned human DNA inserts will be labeled in situ with their vector sequences by primer extension (Feinberg and Vogelstein (1983); Anal. Biochem, 132:6–13). For hybridization to membrane with NF1-YAC DNAs which carry plasmid sequences homologous to many of the probes, the human DNA insert will be isolated from the probe vector by restriction enzyme digestion, electrophoresis and recovery on NA 45 DEAE membrane (Schliecher and Schueel, Keene, N.H.) before labeling. Hybridization will be as previously described (Donis-Deller et al. (1987); Cell, 51:319–337).

Linkage analysis. Two-point and multipoint linkage analyses will be performed with the program CRI-MAP Version 24 (Barker et al. (1987); P. N. A. S., USA, 84:8006–8010). The ALL option of the program will be used to calculate the likelihood that the M17S1 locus mapped in any one marker interval on a map of 15 pericentromeric loci.

According to the above-described protocol, linkage studies of the ESA gene may be conducted. ESA gene defects may also be detected as a Pst 1 polymorphism employing the above-described method.

EXAMPLE 9

THE HUMAN GENE FOR AN EPIDERMAL SURFACE ANTIGEN (M17S1) IS LOCATED AT 17O11-12[1]

The cDNA for a novel epidermal surface antigen, ESA, has recently been isolated (Schroeder et al. 1990). The function of this antigen is unknown at present, but it does not share significant homology to other cell surface receptors or molecules. We report here the chromosomal and regional localization of the ESA gene, M17S1, to the long arm of chromosome 17 in the region containing the locus for von Recklinghausen neurofibromatosis (NF1) (Wallace et al., 1990; Viskochil et al. 1990).

Chromosomal assignment of the ESA gene was made by screening a well-characterized human somatic cell/Chinese hamster ovary panel informative for all human chromosomes (Stallings et al. 1988) with the 2.0 kb ESA cDNA insert. Hybridization of oligolabeled (Feinberg and Vogelstein, 1983) ESA cDNA to Southern blots (Southern, 1975) of HindIII-digested DNA from human/Chinese hamster hybrids detected a 7.5 kb human fragment which was easily resolved from the 4.3 kb CHO fragment. Concordant segregation analysis revealed 0% discordance between the ESA gene and human chromosome 17 markers, whereas the level of discordancy between the ESA and markers for every other human chromosome ranged from 47 to 57% discordancy. Therefore the ESA gene was assigned to human chromosome 17.

Figure 6:
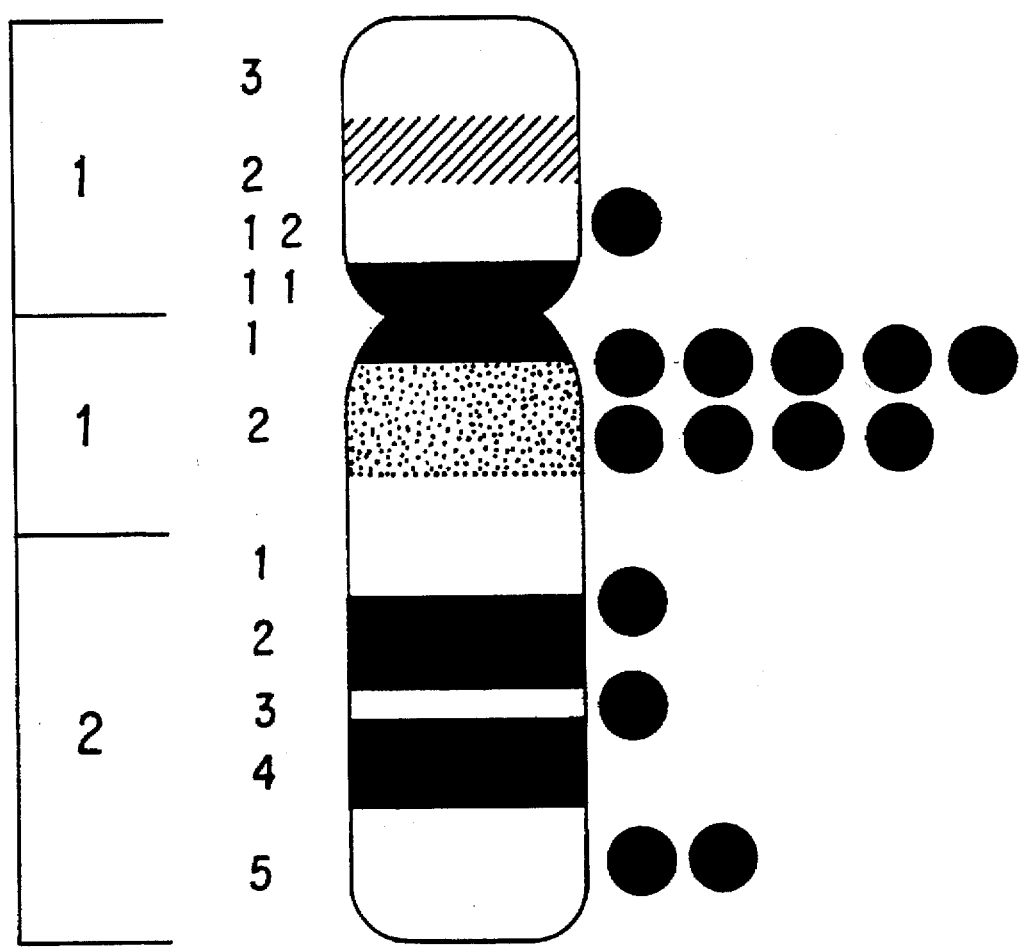
FIG. 6—Idiogram of Chromosome 17 displaying 64% of label on segment 17q11.2

Regional assignment of the ESA gene was accomplished by in situ hybridization of human prometaphase chromosomes with the ESA cDNA at concentrations of 12–25 ng/ml as previously described (Schroeder et al., 1984). Analysis of 70 labeled sites demonstrated significant labeling of the proximal portion of the long arm of chromosome 17. Of the cells analyzed, 44% displayed labeling of chromosome 17. Detailed analysis of chromosome 17 demonstrated that 64% of the labeled sites of chromosome 17 were in the region 17q11-12 (FIG. 6), representing 13% of all observed labeling. Three percent was the highest percentage of labeling on any other chromosomal region due to nonspecific hybridization of the cDNA.

These results map a novel gene for an epidermal surface antigen to chromosome region 17q11-12. It is interesting that the ESA gene lines in the same region as NF1, as disease of tissues derived from the neural crest, which involves such dermatologic disorders as cafe-au-lait spots, dermal neurofibromas, axillary freckling, and hyperpigmentation. Whether there exists any relationship between the ESA gene and NF1 locus is not known at this time, but the localization of the ESA gene to the same region as NF1 may not be inconsequential in view of all the epithelial lesions involved in NF1 (Riccardi, 1980). As more genes involved in epidermal differentiation and maintenance are isolated and mapped, a better understanding of diseases that interrupt or destroy these processes will become possible.

EXAMPLE 10

ESA & IN EPITHELIAL CELL STRUCTURE AND FUNCTION

To demonstrate directly that ESA is involved in cell-cell adhesion, stably transfected mouse fibroblasts cell lines have been established by transfection with the full-length ESA cDNA. The full-length ESA cDNA was subcloned into eukaryotic expression vector pSG5 and transfected by the DEAE-dextran method into mouse L cell fibroblasts (Selden R. F. (1992), Transfection using DEAE-Dextran. In Current Protocols in Molecular Biology (F. M. Ausbel, R. Brent, R. E. Kingston, D. D. Publishing Associates and Wiley-Interscience, John Wiley & sons, New York), which reference is specifically incorporated herein by reference for this purpose. The plasmid encoding the neomycin resistance gene pSV2neo was cotransfected with the ESA expression plasmid and stable cells selected by growth in G418. After ten days in G418-supplemented media, individual resistant cells were isolated and grown in 100 mm culture dishes. Transfected cells expressing high levels of ESA protein become morphologically transformed forming tight intercellular junctions as opposed to nontransfected cells or cells transfected with vector alone which do not form tight intercellular connections in monolayer cultures. Furthermore, transfected cells changed from spindle or round shapes to a polygonal closely linked "epithelioid" sheet when grown to confluence.

These studies provide direct support that the novel epidermal surface antigen, ESA, is important for normal epidermal adhesion.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. Changes in DNA and protein sequences may also be made without affecting in kind or amount the biological action of such molecules. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

1. Beutner, E. H. et al. (1965) *JAMA* 192:682–688.
2. Beutner, E. H. et al. (1968) *J. Invest. Dermatol.*, 51:63–80.
3. Jordan, R. E. et al. (1971) *Arch. Dermatol.*, 103:486–491.
4. Jordon, R. E. (1991) *Immunologic Diseases of the Skin* (Appleton & Lange, East Norwalk, Conn.)
5. Sams, W. M. J. and Jordon, R. E. (1971) *Br. J. Dermatol.*, 84:7–13.
6. Schiltz, J. R. and Michel, B. (1976) *J. Invest. Dermatol.*, 67:254–260.
7. Wood, G. W. and Beutner, E. H. (1977) *Clin. Immunol. Immunopathol.*, 7:168–175.
8. Merlob, P. et al. (1986), *Pediatrics*, 78:1102–1105.
9. Stanley, J. R. et al. (1988) *J. Clin. Invest.*, 82:1864–1870.
10. Tanaka, T. et al. (1991) *J. Biol. Chem.*, 266:12555–12559.
11. Amagai, M. et al. (1991) *Cell*, 67:869–877.
12. Korman, N. J. et al. (1989) *N. Engl. J. Med.*, 321:631–635.
13. Negi, M. et al. (1986) *J. Invest. Dermatol.*, 86:634–637.
14. Schroeder, W. T. et al. (1991) *Genomics*, 11:481–482.
15. Young, R. A. and Davis, R. W. (1983) *Science*, 222:778–782.
16. Young, R. A. and Davis, R. W. (1983) *Proc. Natl. Acad. Sci. USA*, 80:1194–1198.
17. Sanger, F. et al. (1977) *Proc. Natl. Acad. Sci. USA*, 74:5463–5467.
18. Devereux, J. et al. (1984) *Nucl. Acids Res.*, 12:387–395.
19. Brutlag, D. L. et al. (1990) *CABIOS*, 6:237–245.
20. Kyte, J. and Doolittle, R. F. (1982) *J. Mol. Biol.*, 157:105–132.
21. Weinberger, C. et al. (1985) *Science*, 228:740–742.
22. Harper, M. E. and Marselle, L. M. (1987) *Methods Enzymol.*, 151:539–551.
23. Davis, L. G. et al. (1986) in *Basic Methods in Molecular Biology*, eds. Davis, L. G., Dibner, M. D. & Battery, J. F. (Elsevier Science Publishing, New York), 1st Ed.: pp. 130–135.
24. Maniatis, T., Fritsch, E. F. and Sambrook, J. (eds.) (1982) *Molecular Cloning a Laboratory Manual* (Cold Spring Harbor Laboratory, Cold Spring Harbor, N.Y.), 1st Ed., Vol. 1.
25. Southern, E. M. (1975) *J. Mol. Biol.*, 98:503–517.
26. Kozak, M. (1987) *Nucl. Acids Res.*, 15:8125–8148.
27. Tokunaga, K. et al. (1987) *Can. Res.*, 47:5616–5619.
28. Hashimoto, K. et al. (1966) *J. Invest. Dermatol.*, 47:317–335.
29. Matsunake, M. and Mishima, Y. (1969) *Acta. Derm. Venerol (Stockh)*, 49:241–250.
30. Garrod, D. R. (1986) *J. Cell Sci. Suppl.*, 4:221–237.
31. Katz, A. M. et al. (1991) *Intern. J. Derm.*, 30:153–160.
32. Caughman, S. W. (1991) *Prog. Dermatol.*, 25:1–8.
33. Horwitz, A. et al. (1986) *Nature*, 320:531–533.
34. Burridge, K. et al. (1988) *Ann. Rev. Cell Biol.*, 4:487–525.

---

What is claimed is:

1. An isolated nucleic acid segment encoding an epidermal surface antigen nucleic acid segment having a sequence as defined in SEQ ID NO:2.

2. The nucleic acid segment of claim 1, further defined as a cDNA.

3. The nucleic acid segment of claim 2, wherein the cDNA is cloned into pGEM-3Z vector.

4. A recombinant vector comprising a nucleic acid segment of claim 1 or 2.

5. A recombinant host cell incorporating a nucleic acid segment of claim 1 or 2.

6. The recombinant host cell of claim 5, further defined as a eukaryotic host cell.

7. The recombinant host cell of claim 5, further defined as a bacterial host cell.

8. The recombinant host cell of claim 6, wherein the nucleic acid segment is integrated into the genome of the host cell.

9. The recombinant host cell of claim 5, wherein the nucleic acid segment is cloned on a recombinant vector.

10. The recombinant host cell of claim 9, wherein the recombinant vector is pSG5.

11. The recombinant host cell of claim 5, wherein the host cell express the epidermal surface antigen.

12. An isolated human epidermal surface antigen gene as defined by the sequence of nucleotides from positions 127 to 1263 of SEQ ID NO:2, or a nucleotide sequence fully complementary thereto.

13. A DNA molecule having a sequence of clone pESA 2.0.

14. A pESA 2.0 clone.

15. A DNA molecule having a sequence of pESA 2.5 clone.

16. A pESA 2.5 clone.

17. An isolated nucleic acid molecule having a nucleotide sequence fully complementary to SEQ ID NO:2.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
      ( A ) LENGTH: 379 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:1:

```
Met  Thr  Leu  Gln  Pro  Arg  Cys  Glu  Asp  Val  Glu  Thr  Ala  Glu  Gly  Val
 1                  5                            10                           15

Ala  Leu  Thr  Val  Thr  Gly  Val  Ala  Gln  Val  Lys  Ile  Met  Thr  Glu  Lys
               20                           25                           30

Glu  Leu  Leu  Ala  Val  Ala  Cys  Glu  Gln  Phe  Leu  Gly  Leu  Asn  Val  Gln
               35                           40                           45

Asp  Ile  Lys  Asn  Val  Val  Leu  Gln  Thr  Leu  Glu  Gly  His  Leu  Arg  Ser
          50                           55                           60
```

| | | | | | | | | | | | | | | | |
|---|---|---|---|---|---|---|---|---|---|---|---|---|---|---|---|
|Ile|Leu|Gly|Thr|Leu|Thr|Val|Glu|Gln|Ile|Tyr|Gln|Asp|Arg|Asp|Gln|
|65| | | | |70| | | |75| | | | | |80|
|Phe|Ala|Lys|Leu|Val|Arg|Glu|Val|Ala|Ala|Pro|Asp|Val|Gly|Arg|Met|
| | | | |85| | | | |90| | | | |95| |
|Gly|Ile|Glu|Ile|Leu|Ser|Phe|Thr|Ile|Lys|Asp|Val|Tyr|Asp|Lys|Val|
| | | |100| | | | |105| | | | |110| | |
|Asp|Tyr|Leu|Ser|Ser|Leu|Gly|Lys|Thr|Gln|Thr|Ala|Val|Val|Gln|Arg|
| | | |115| | | | |120| | | | |125| | |
|Asp|Ala|Asp|Ile|Gly|Val|Ala|Glu|Ala|Glu|Arg|Asp|Ala|Gly|Ile|Arg|
| | |130| | | | |135| | | | |140| | | |
|Glu|Ala|Glu|Cys|Lys|Lys|Glu|Met|Leu|Asp|Val|Lys|Asp|Met|Ala|Asp|
|145| | | | |150| | | |155| | | | | |160|
|Thr|Lys|Ile|Ala|Asp|Ser|Lys|Arg|Ala|Phe|Glu|Leu|Gln|Lys|Ser|Ala|
| | | | |165| | | | |170| | | | |175| |
|Phe|Ser|Glu|Glu|Val|Asn|Ile|Lys|Thr|Ala|Glu|Ala|Gln|Leu|Ala|Tyr|
| | | |180| | | | |185| | | | |190| | |
|Glu|Leu|Gln|Gly|Ala|Arg|Glu|Gln|Gln|Lys|Ile|Arg|Gln|Glu|Glu|Ile|
| | | |195| | | | |200| | | | |205| | |
|Glu|Ile|Glu|Val|Val|Gln|Arg|Lys|Lys|Gln|Ile|Ala|Val|Glu|Ala|Gln|
| | |210| | | | |215| | | | |220| | | |
|Glu|Ile|Leu|Arg|Thr|Asp|Lys|Glu|Leu|Ile|Ala|Thr|Val|Arg|Arg|Pro|
|225| | | | |230| | | |235| | | | | |240|
|Ala|Glu|Ala|Glu|Ala|His|Arg|Ile|Gln|Gln|Ile|Ala|Glu|Gly|Glu|Lys|
| | | | |245| | | | |250| | | | |255| |
|Val|Lys|Gln|Val|Leu|Leu|Ala|Gln|Ala|Glu|Ala|Glu|Lys|Ile|Arg|Lys|
| | | |260| | | | |265| | | | |270| | |
|Ile|Gly|Glu|Ala|Glu|Ala|Ala|Val|Ile|Glu|Ala|Met|Gly|Lys|Ala|Glu|
| | |275| | | | |280| | | | |285| | | |
|Ala|Glu|Arg|Met|Lys|Leu|Lys|Ala|Glu|Ala|Tyr|Gln|Lys|Tyr|Gly|Asp|
| |290| | | | |295| | | | |300| | | | |
|Ala|Ala|Lys|Met|Ala|Leu|Val|Leu|Glu|Ala|Leu|Pro|Gln|Ile|Ala|Ala|
|305| | | | |310| | | |315| | | | | |320|
|Lys|Ile|Ala|Ala|Pro|Leu|Thr|Lys|Val|Asp|Glu|Ile|Val|Val|Leu|Ser|
| | | | |325| | | | |330| | | | |335| |
|Gly|Asp|Asn|Ser|Lys|Val|Thr|Ser|Glu|Val|Asn|Arg|Leu|Leu|Ala|Glu|
| | | |340| | | | |345| | | | |350| | |
|Leu|Pro|Ala|Ser|Val|His|Ala|Leu|Thr|Gly|Val|Asp|Leu|Ser|Lys|Ile|
| | | |355| | | | |360| | | | |365| | |
|Pro|Leu|Ile|Lys|Lys|Ala|Thr|Gly|Val|Gln|Val| | | | | |
| |370| | | | |375| | | | | | | | | |

( 2 ) INFORMATION FOR SEQ ID NO:2:

( i ) SEQUENCE CHARACTERISTICS:
        ( A ) LENGTH: 2488 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
CGGCCCAACG AGGCGCTGGT GGTTTCAGGG GGCTGTTGTG GTTCCGACTA TAAACAGTAC      60
GTGTTTGGCG GCTGGGCCTG GGCCTGGTGG TGTATCTCCG ACACTCAGAG GATTTCCCTA     120
GAGATTATGA CGTTGCAGCC CCGCTGCGAG GACGTAGAGA CGGCCGAGGG GGTAGCTTTA     180
ACTGTGACGG GTGTCGCCCA GGTGAAGATC ATGACGGAGA AGGAACTCCT GGCCGTGGCT     240
```

-continued

```
TGTGAGCAGT TTCTGGGTAA GAATGTGCAG GACATCAAAA ACGTCGTCCT GCAGACCCTG      300
GAGGGACATC TGCGCTCCAT CCTCGGGACC CTGACAGTGG AGCAGATTTA TCAGGACCGG      360
GACCAGTTTG CCAAGCTGGT GCGGGAGGTG GCAGCCCTG ATGTTGGCCG CATGGGCATT       420
GAGATCCTCA GCTTCACCAT CAAGGACGTG TATGACAAAG TGGACTATCT GAGCTCCTG      480
GGCAAGACGC AGACTGCCGT GGTGCAGAGA GATGCTGACA TTGGCGTGGC CGAGGCTGAA      540
CGGGACGCAG GCATCCGGGA AGCTGAGTGC AAGAAGGAGA TGCTGGATGT GAAGTTCATG      600
GCAGACACCA AGATTGCTGA CTCTAAGCGA GCCTTCGAGC TGCAAAAGTC AGCCTTCAGT      660
GAGGAGGTTA ACATCAAGAC AGCTGAGGCC CAGTTGGCCT ATGAGCTGCA GGGGGCCCGT      720
GAACAGCAGA AGATCCGGCA GGAAGAGATT GAGATTGAGG TTGTGCAGCG CAAGAAACAG      780
ATTGCCGTGG AGGCACAGGA GATCCTGCGT ACGGACAAGG AGCTCATCGC TACAGTGCGC      840
CGGCCTGCCG AGGCCGAGGC CCACCGCATC CAGCAGATTG CCGAGGGTGA AAAGGTGAAG      900
CAGGTCCTCT TGGCACAGGC AGAGGCTGAG AAGATCCGCA AAATCGGGGA GGCGGAAGCG      960
GCAGTCATCG AGGCGATGGG CAAGGCAGAG CTGAGCGGA TGAAGCTCAA GGCAGAAGCC     1020
TACCAGAAAT ACGGGGATGC AGCCAAGATG GCCTTGGTGC TAGAGGCCCT GCCCCAGATT     1080
GCTGCCAAAA TCGCTGCCCC ACTTACCAAG GTCGATGAGA TTGTGGTCCT CAGTGGAGAC     1140
AACAGTAAGG TCACATCAGA AGTGAACCGA CTGCTGGCCG AGCTGCCTGC CTCTGTGCAT     1200
GCCCTCACAG GCGTGGACCT GTCTAAGATA CCCCTGATCA AGAAGGCCAC TGGTGTGCAG     1260
GTGTGAGGCT CCTACAGGCC CACTCTCTTC AGCAGCCACC CGGCCCTCCC TCCAGCACCC     1320
GTTTTAATCC CACAGAACAA CGGGAACGTT ACTGACTCTG GTGCCTTATC TCGAAGGGAC     1380
CAGAAGTGCT GCGTGTTCAG GCCATCTCTG GCTGTCTTCC TGTCTCTCCT GTCTGTCCAC     1440
CTCCTCCTCT TCCTCTCCTT TACCCCACTT TCACTGCCAC TTTCATCAGG TTTGTGTCTC     1500
ATCTCCCTGC GTGTCTTTTC CTTTGTCTGT CTTTTCTTT CCCCCATGCA CATCATGTAG      1560
ATTAAGCTGA AGATGTTTAT TACAATCACT CTCTGTGGGG GGTGGCCCTG CTGCTCCTCA     1620
GAATCCTGGT GCCTTGAAGT TCTCTGTGCA TCTGTCCATC CTCCCTATGG CCCTGGCCAG     1680
AGCTCAGCAT GGGCAGGGGT TCTGGGTAGG ACGGTCACTG TCCTCTCTCC TGGACTGGTC     1740
TTCCCAGCCC TAAACCCTGC CCCAGGAAGC CCACAGCCTC ACCTGCTGCT GCCCCTCTAG     1800
GTCTGGGCAG CCATGACCTG CAGGGCCCAG AGACACTGTC CTTCCCCTCA TCCACCCAAG     1860
GCCCCAGCCA GCGCTCATAC CCTGTCCTTT CTCCCTGACC CCAAGGGCAC AGAGGCAAGG     1920
CCTCCTGTCT ACAGCAGCTT CCTCAGTTTC CTACTGCCTT AGGAGGCCCC TGCTTGTGCT     1980
CAGGGAAGGC CTCTTCATGG GCATGTTCCT GCTGGGGCGG TGCGGTTTGG TCCCAACTCT     2040
GCTAAGTTTT CTGAGATGAG GGTCTAGCCC TGTTGGGGAC AGAAAAGTGT GTAGACCTTC     2100
TTCCTGCTAG GGCTGCACTG TCCTGGGTGT TGGGCCCTTC TGGTGGACAA GGCTGTGCCA     2160
ACCCTGTACA GAATCGAGTG CTGTAGCCTG GCCAGACCCC AGAGCCCTTG TGCCATCTTT     2220
CTTCCTGGCC AGAGTGATGG GGTTCCAGCC ATGGGAAGC AACCCAATCC TCTGTCTCCT      2280
TGCTCCAATG GAGGCAGAAG AGCCCAGGAC CCAAGCGTCT TGGCAGGGGT GCTGTGAATG     2340
TCCAGTGGTC CCAGCTCCCC ACCCTGGCCC TGCCCAGCC TGTGTAGCTC TTCCTGCATG      2400
TGGATGCTGC ATGTCTGGTC TGGGGCTTGG ATGTTGCACT GCCCACTGC CTGTCCCTTC      2460
TGGTAAAATA AAGAACTCTT AATGCCCG                                        2488
```

( 2 ) INFORMATION FOR SEQ ID NO:3:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:3:

GNNGNNANNA TG         12